United States Patent
Winter

(10) Patent No.: US 12,168,005 B2
(45) Date of Patent: Dec. 17, 2024

(54) METHODS FOR TREATING WILD TYPE ISOCITRATE DEHYDROGENASE 1 CANCERS

(71) Applicant: University Hospitals Cleveland Medical Center, Cleveland, OH (US)

(72) Inventor: Jordan M. Winter, Shaker Heights, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 462 days.

(21) Appl. No.: 17/030,844

(22) Filed: Sep. 24, 2020

(65) Prior Publication Data

US 2021/0100780 A1  Apr. 8, 2021

Related U.S. Application Data

(60) Provisional application No. 62/911,717, filed on Oct. 7, 2019.

(51) Int. Cl.
| | | |
|---|---|---|
| *A61K 31/444* | (2006.01) | |
| *A61P 35/00* | (2006.01) | |
| *G01N 33/50* | (2006.01) | |
| *A61K 45/06* | (2006.01) | |

(52) U.S. Cl.
CPC ............ *A61K 31/444* (2013.01); *A61P 35/00* (2018.01); *G01N 33/5038* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,851,789 A | 12/1998 | Simon et al. | 435/32 |
| 6,238,878 B1 | 5/2001 | Jakobsen et al. | 435/13 |
| 6,632,979 B2 | 10/2003 | Erickson et al. | 800/18 |
| 6,905,839 B2 | 6/2005 | Furuta | 435/29 |
| 9,662,327 B2 | 5/2017 | Cao et al. | |
| 9,850,277 B2 | 12/2017 | Popovici-Muller et al. | |
| 9,968,595 B2 | 5/2018 | Gu | |
| 2013/0190249 A1 | 7/2013 | Lemieux et al. | 514/19.3 |
| 2016/0137585 A1 | 5/2016 | Chen et al. | 424/85.2 |
| 2017/0014396 A1 | 1/2017 | Gu | |
| 2018/0071302 A1 | 3/2018 | Abella et al. | |
| 2018/0296583 A1 | 10/2018 | Agresta et al. | |
| 2018/0353514 A1 | 12/2018 | Murtie et al. | |
| 2019/0046512 A1 | 2/2019 | Amatangelo et al. | |
| 2019/0076425 A1 | 3/2019 | Srinivasan et al. | |
| 2019/0133980 A1 | 5/2019 | Bindra et al. | |
| 2022/0280538 A1* | 9/2022 | Lowe | A61K 31/51 |

FOREIGN PATENT DOCUMENTS

WO  WO2019012328 A1  1/2019

OTHER PUBLICATIONS

Merchant et al., Ivosidenib: IDHI Inhibitor for the Treatment of Acute Myeloid Leukemia. Journal of the Advanced Practitioner in Oncology, 2019, 10, 494-500.*
Grant & Hackh's Chemical Dictionary (5th Ed. 1987) at p. 148.*
Bergaggio and Piva, "Wild-Type IDH Enzymes as Actionable Targets for Cancer Therapy." *Cancers*, 11(4):563 pp. 1-16 (2019).
Brody, et al., "Identification of a Novel Metabolic-Related Mutation (IDH1) in Metastatic Pancreatic Cancer." *Cancer Biology & Therapy*: 19(4):249-253 (2018), pp. 1-5 (2016).
Deng, et al., "Selective Inhibition of Mutant Isocitrate Dehydrogenase 1 (IDH1) Via Disruption of a Metal Binding Network by an Allosteric Small Molecule." *J Biol Chem*, 290(2):762-774 (2015).
Fuhrmann, et al., "Metastatic State of Cancer Cells May Be Indicated by Adhesion Strength." *Biophys J*, 112(4):736-745 (2017).
Itsumi, et al., "IDH1 Protects Murine Hepatocytes from Endotoxin-Induced Oxidative Stress by Regulating the Intracellular NADP(+)/NADPH Ratio." *Cell Death Differ*, 22(11):1837-1845 (2015).
Kamphorst, et al., "Human Pancreatic Cancer Tumors Are Nutrient Poor and Tumor Cells Actively Scavenge Extracellular Protein." *Cancer Research*, 75(3):544-553 (2015).
Lin, et al., "Discovery and Optimization of Quinolinone Derivatives as Potent, Selective, and Orally Bioavailable Mutant Isocitrate Dehydrogenase 1 (MIDH1) Inhibitors." *J Med Chem*, 62(14):6575-6596, pp. 1-22 (A-V) (2019).
Ma, et al., "Inhibitors of Mutant Isocitrate Dehydrogenases 1 and 2 (MIDH1/2): An Update and Perspective." *J Med Chem*, 61(20): 8981-9003, pp. 1-79 (2018).
Nicolay, et al., "The IDH1 Mutant Inhibitor Ag-120 Shows Strong Inhibition of 2-HG Production in an Orthotopic IDH1 Mutant Glioma Model in Vivo." Presented at the Society of Neuro-Oncology, San Francisco. Abstract and poster—each 1 page, (2017).
Popovici-Muller, et al., "Discovery of Ag-120 (Ivosidenib): A First-in-Class Mutant IDH1 Inhibitor for the Treatment of IDH1 Mutant Cancers." *ACS Med Chem Lett*, 9(4):300-305 (2018).
Seltzer, et al., "Serum and Tissue Magnesium Levels in Human Breast Carcinoma." *J Surg Res*, 10(4):159-162 (1970).
Sun, et al., "A Systematic Analysis of FDA-Approved Anticancer Drugs." *BMC Systems Biology*, 11(5):87 pp. 27-43 (2017).
Urban, et al., "Assessing Inhibitors of Mutant Isocitrate Dehydrogenase Using a Suite of Pre-Clinical Discovery Assays." *Scientific reports*, 7(1):12758 pp. 1-15 (2017).

(Continued)

*Primary Examiner* — Po-Chih Chen
(74) *Attorney, Agent, or Firm* — Medlen & Carroll, LLP

(57) ABSTRACT

The invention provides methods of treating cancer characterized by the presence of one or both of wild type isocitrate dehydrogenase 1 (IDH1) gene and wild type IDH1 enzyme, by administering compounds that inhibit mutant IDH1 enzyme, such as Ivosidenib (AG-120, IVOSIDENIB®). The invention also provides cell-based methods for determining anti-cancer activity of test compounds under in vitro conditions of low concentrations of magnesium ion and/or glucose.

13 Claims, 18 Drawing Sheets

Specification includes a Sequence Listing.

(56) References Cited

OTHER PUBLICATIONS

Zarei, et al., "Posttranscriptional Upregulation of IDH1 by HUR Establishes a Powerful Survival Phenotype in Pancreatic Cancer Cells." *Cancer Research*, 77(16):4460-4471 (2017).
Zarei, et al., "RNA-Binding Protein HUR Regulates Both Mutant and Wild-Type IDH1 in IDH1-Mutated Cancer." *Mol Cancer Res*, 17(2):508-520 (2019).
Ziebart, et al., "Metabolic and Proteomic Differentials in Head and Neck Squamous Cell Carcinomas and Normal Gingival Tissue." *J Cancer Res Clin Oncol.*, 137(2):193-199 (2011).
Gyorkey, et al., "Zinc and Magnesium in Human Prostate Gland: Normal, Hyperplastic, and Neoplastic." Cancer Research, 27(8):1348-1353 (1967).

\* cited by examiner

FIG. 1A                    FIG. 1B
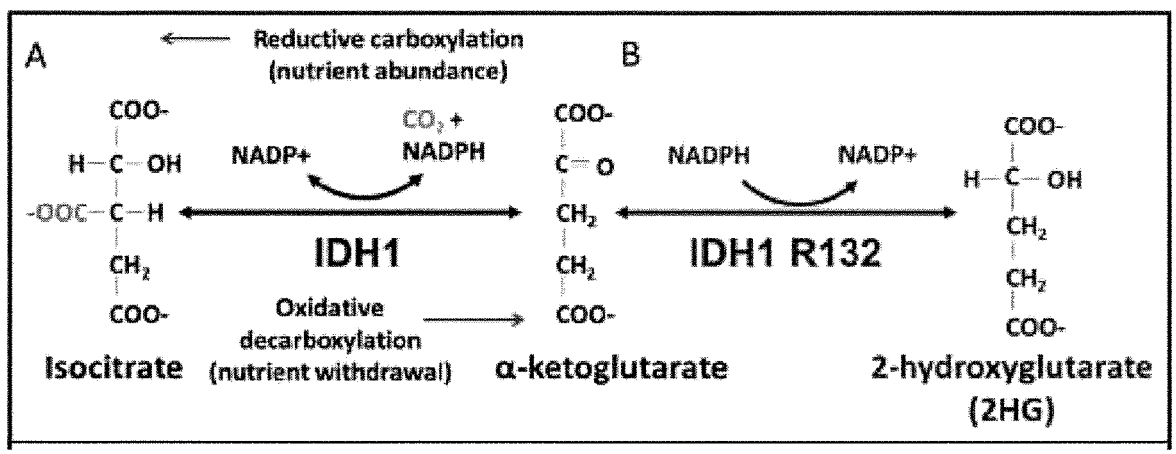

FIG. 2A
FIG. 2B
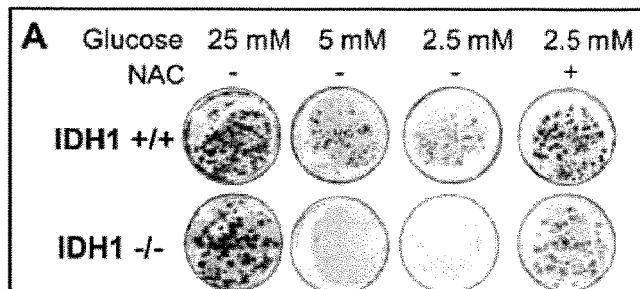
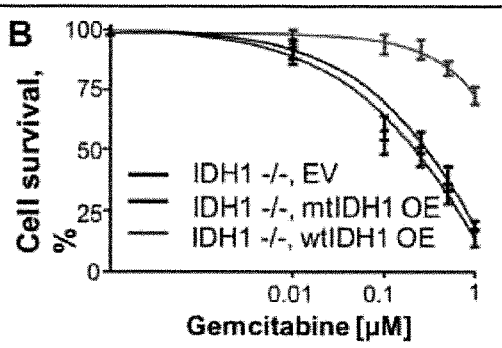
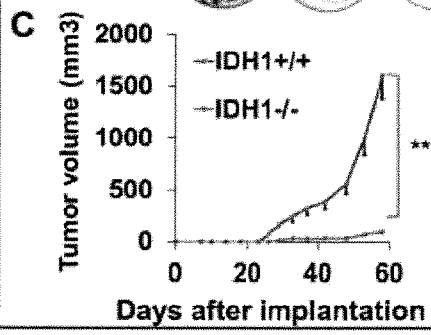
FIG. 2C

FIG. 3A
FIG. 3B
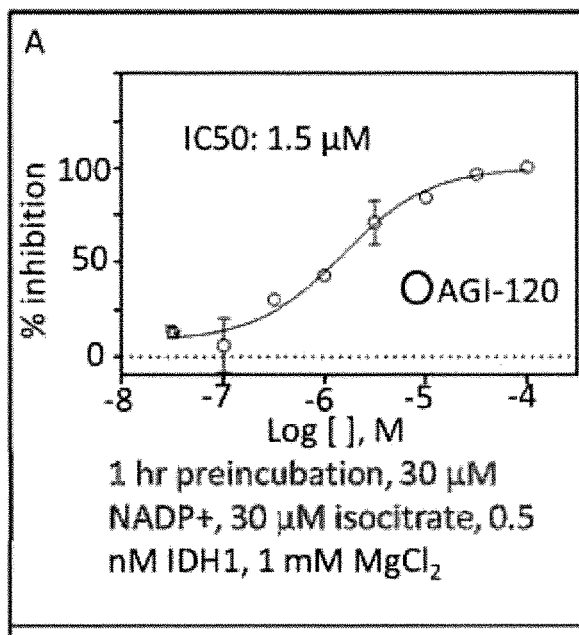
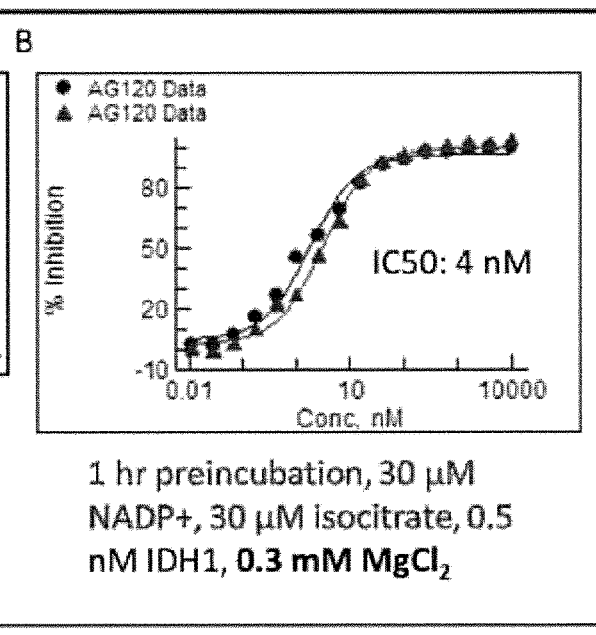

AG-120

AG-5198

Agios 135

ML309

Novartis 224

Novartis 224

Novartis 530

GSK864

Sanofi 1

AGI-6780

AG-221

IDH2-C100

14 (GSK321)

19 (BAY-1436032)

IDH305          IDH305

DS1001

FIG. 9A
(S)-N-((S)-1-(2-chlorophenyl)-2-((3,3-difluorocyclobutyl)amino)-2-oxoethy-1)-1-(4-cyanopyridin-2-yl)-N-(5-fluoropyridin-3-yl)-5-oxopyrrolidine-2-carboxamide
FIG. 9B
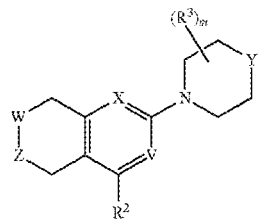
FIG. 9C
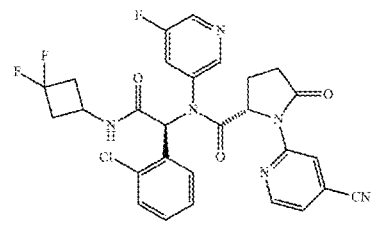
FIG. 9D
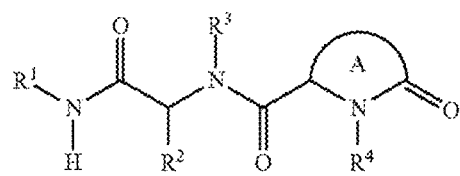
FIG. 9E
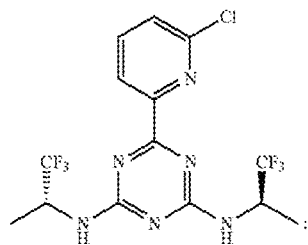

Human wild type IDH1 amino acid sequence (SEQ ID NO:01) listed at GenBank NCBI Reference Sequence: NM_005896.3

```
1    MSKKISGGSV VEMQGDEMTR IIWELIKEKL IFPYVELDLH   40
41   SYDLGIENRD ATNDQVTKDA AEAIKKHNVG VKCATITPDE   80
81   KRVEEFKLKQ MWKSPNGTIR NILGGTVFRE AIICKNIPRL   120
121  VSGWVKPIII GRHAYGDQYR ATDFVVPGPG KVEITYTPSD   160
161  GTQKVTYLVH NFEEGGGVAM GMYNQDKSIE DFAHSSFQMA   200
201  LSKGWPLYLS TKNTILKKYD GRFKDIFQEI YDKQYKSQFE   240
241  AQKIWYEHRL IDDMVAQAMK SEGGFIWACK NYDGDVQSDS   280
281  VAQGYGSLGM MTSVLVCPDG KTVEAEAAHG TVTRHYRMYQ   320
321  KGQETSTNPI ASIFAWTRGL AHRAKLDNNK ELAFFANALE   360
361  EVSIETIEAG FMTKDLAACI KGLPNVQRSD YLNTFEFMDK   400
401  LGENLKIKLA QAKL                               414
```

FIG. 10

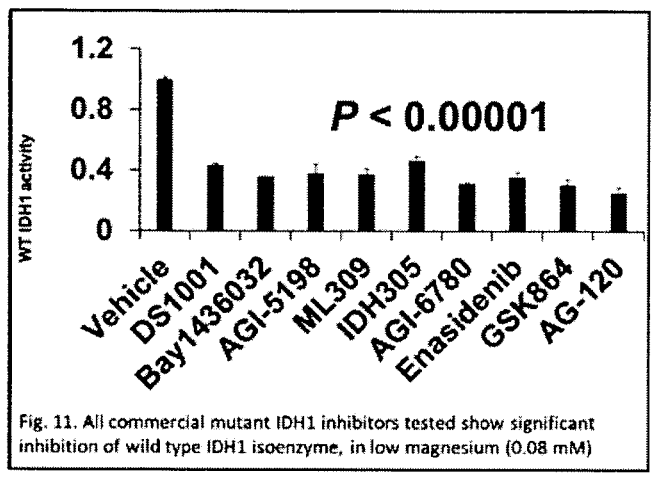
Fig. 11. All commercial mutant IDH1 inhibitors tested show significant inhibition of wild type IDH1 isoenzyme, in low magnesium (0.08 mM)
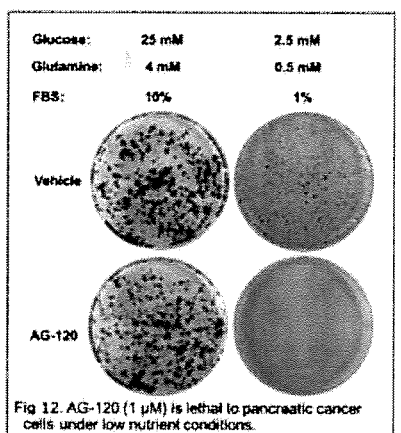
Fig 12. AG-120 (1 µM) is lethal to pancreatic cancer cells under low nutrient conditions.
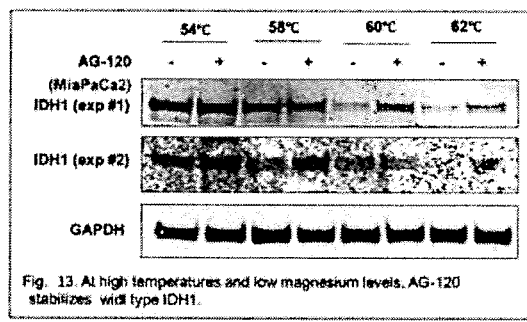
Fig. 13. At high temperatures and low magnesium levels, AG-120 stabilizes wild type IDH1.

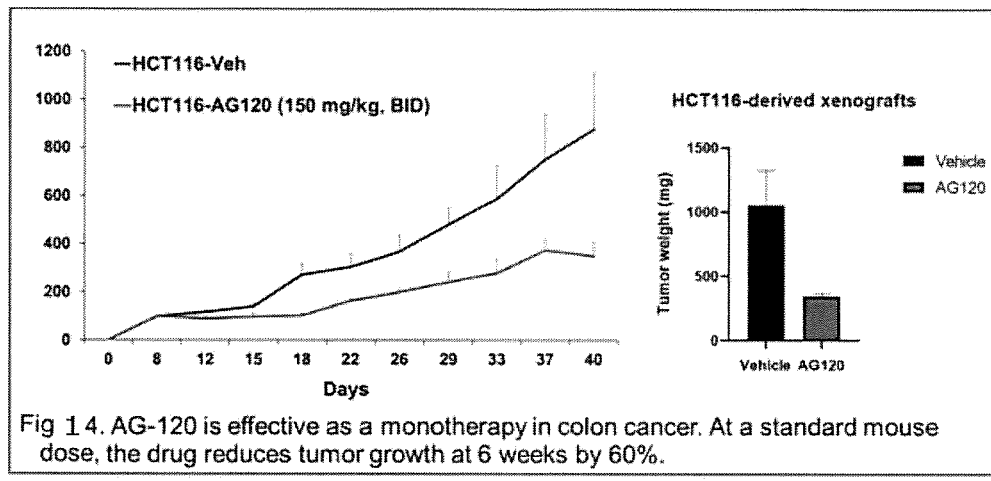
Fig 14. AG-120 is effective as a monotherapy in colon cancer. At a standard mouse dose, the drug reduces tumor growth at 6 weeks by 60%.
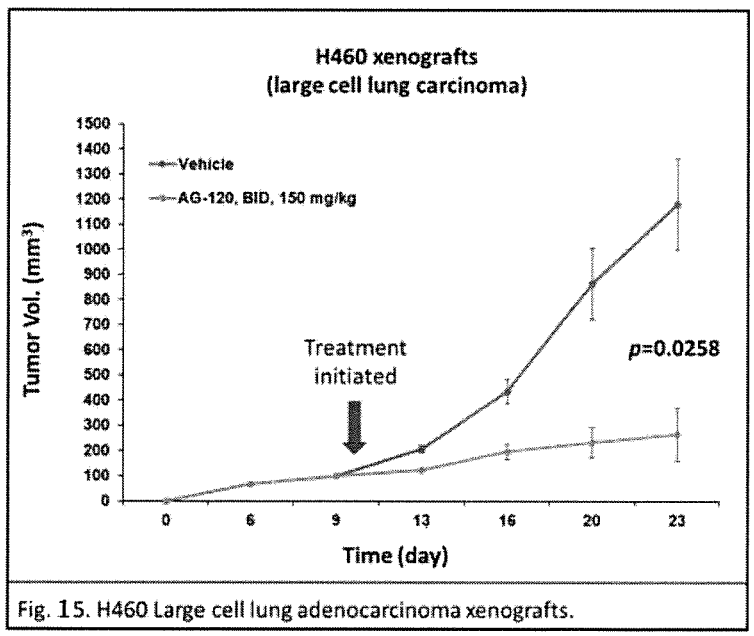
Fig. 15. H460 Large cell lung adenocarcinoma xenografts.

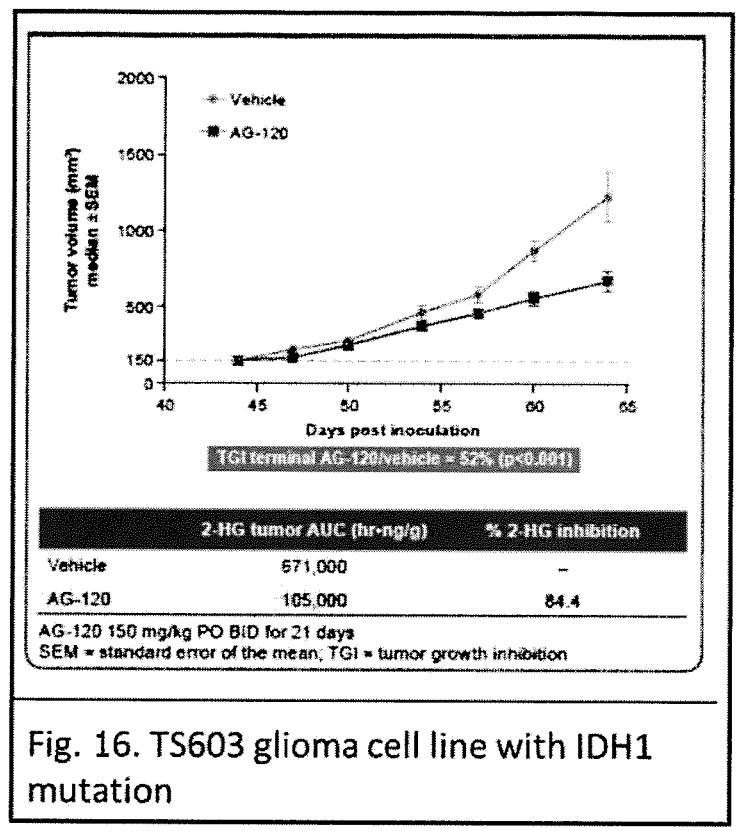
Fig. 16. TS603 glioma cell line with IDH1 mutation

METHODS FOR TREATING WILD TYPE ISOCITRATE DEHYDROGENASE 1 CANCERS

This application claims priority to U.S. provisional Patent Application Ser. No. 62/911,717 filed on Oct. 7, 2019, incorporated by reference.

GOVERNMENT INTEREST

This invention was made with government support under grant number R37CA227865-01A1 awarded by the National Institutes of Health (NIH). The government has certain rights in the invention.

A Sequence Listing has been submitted in an ASCII text file named "19708.txt" created on Nov. 20, 2020 consisting of 3.84 bytes, the entire content of which is herein incorporated by reference.

FIELD OF THE INVENTION

The invention provides methods of treating cancer characterized by the presence of one or both of wild type isocitrate dehydrogenase 1 (IDH1) gene and wild type IDH1 enzyme, by administering compounds that inhibit mutant IDH1 enzyme, such as Ivosidenib (AG-120, IVOSIDENIB®). The invention also provides cell-based methods for determining anti-cancer activity of test compounds under in vitro conditions of low concentrations of magnesium ion and/or glucose.

BACKGROUND OF THE INVENTION

Several cancers are characterized by mutations in IDH1 enzyme and have been targeted for treatment using compounds that are tested to specifically target mutant IDH1 enzyme rather than wild type IDH1 enzyme (Urban et al., Sci Rep 2017; 7:12758). However, a large number of cancers express wild type IDH1 gene and/or wild type IDH1 enzyme. Thus, there remains a need for methods of testing compounds that are therapeutic in cancers characterized by the presence of one or both of wild type IDH1 gene and wild type IDH1 enzyme, as well as for using these compounds in cancer treatment.

SUMMARY OF THE INVENTION

In one embodiment, the invention provides a method of treating cancer in a mammalian subject in need thereof, said cancer contains cancer cells characterized by the presence of one or both of wild type isocitrate dehydrogenase 1 (IDH1) gene and wild type IDH1 enzyme, the method comprising the step of administering to said subject a pharmaceutical composition comprising compound AG-120 having the formula

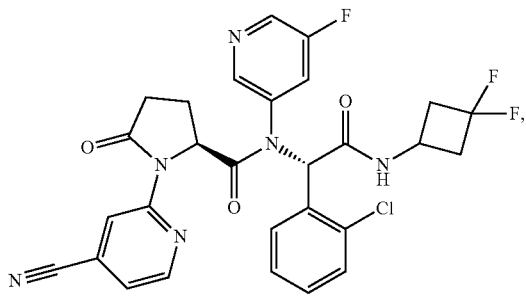 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

said pharmaceutical composition is in a therapeutic amount that reduces wild type IDH1 enzyme activity in said cancer cells. While not intending to limit the cancer to a particular cancer, in one embodiment, cancer comprises one or more of pancreatic cancer, colon cancer, lung cancer and ovarian cancer. In a further embodiment, the wild type IDH1 enzyme comprises amino acid sequence SEQ ID NO:01. In a particular embodiment, the wild type IDH1 enzyme is overexpressed in said cancer cells compared to non-cancerous cells of the same cell type. In another embodiment, the cancer cells lack one or both of mutant IDH1 enzyme and of mutant IDH1 gene. In a further embodiment, one or both of wild type IDH1 gene and wild type IDH1 enzyme is detected in a sample from said subject. In another embodiment, the sample comprises one or both of tissue and bodily fluid. In one embodiment, the method further comprising administering to the subject a second compound comprising an anti-cancer compound that reduces cancer.

The invention also provides a method of treating cancer in a mammalian subject in need thereof, said cancer contains cancer cells characterized by the presence of one or both of wild type isocitrate dehydrogenase 1 (IDH1) gene and wild type IDH1 enzyme, and optionally characterized by the absence of one or both of mutant IDH1 gene and mutant IDH1 enzyme, the method comprising the step of administering to said subject a pharmaceutical composition comprising a first compound that inhibits mutant IDH1 enzyme, said pharmaceutical composition is in a therapeutic amount that reduces wild type IDH1 enzyme activity in said cancer cells. In one embodiment, said first compound that inhibits mutant IDH1 enzyme comprises compound AG-120 having the formula

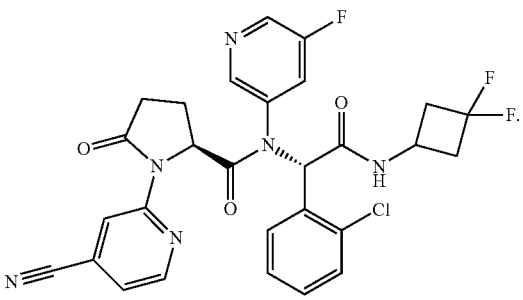 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

In a particular embodiment, said cancer comprises one or more of pancreatic cancer, colon cancer, lung cancer and ovarian cancer. In another embodiment, said wild type IDH1 enzyme is overexpressed in said cancer cells compared to non-cancerous cells of the same cell type. In a further embodiment, said cancer cells lack one or both of mutant IDH1 enzyme and of mutant IDH1 gene. In a particular embodiment, said method further comprising administering to the subject a second compound that reduces cancer. In one embodiment, one or both of wild type IDH1 gene and wild type IDH1 enzyme is detected in a sample from said subject. In a particular embodiment, the method further comprises detecting one or both of wild type IDH1 gene and wild type IDH1 enzyme in said cancer cells. In a further embodiment, sample comprises one or both of tissue and bodily fluid. In one embodiment, the cancer contains cancer cells having a lower Magnesium$^{2+}$ ($Mg^{2+}$) concentration compared to $Mg^{2+}$ concentration in serum, such as serum of said subject and/or serum of a control subject lacking the cancer. In one embodiment, the method further comprises reducing glucose concentration in blood of said subject. In a further embodiment, the method further comprises administering to the subject a compound that competes with glucose by acting as a D-glucose mimic, such as a non-metabolizable glucose analog, exemplified by 2-deoxyglucose (2DG).

The invention also provides a method for determining anti-cancer activity of a test compound, comprising
a) providing
  i) cancer cells characterized by the presence of one or both of wild type isocitrate dehydrogenase 1 (IDH1) gene and wild type IDH1 enzyme,
  ii) culture medium comprising magnesium$^{2+}$ ($Mg^{2+}$) at a concentration lower than 0.5 mM, and
  iii) said test compound,
b) contacting, in vitro, said cancer cells with said culture medium to produce first contacted cells,
c) contacting said first contacted cells with said test compound to produce second contacted cells,
d) measuring wild type IDH1 enzyme activity in said second contacted cells, wherein reduced wild type IDH1 enzyme activity in said second contacted cells compared to said first contacted cells identifies said test compound as having anti-cancer activity.

In one embodiment, said culture medium comprises glucose at a concentration lower than 25 mM. In a particular embodiment, said test compound inhibits mutant IDH1 enzyme activity.

The invention further provides a method for determining anti-cancer activity of a test compound, comprising
a) providing
  i) cancer cells characterized by the presence of one or both of wild type isocitrate dehydrogenase 1 (IDH1) gene and wild type IDH1 enzyme,
  ii) culture medium comprising glucose at a concentration lower than 25 mM, and
  iii) said test compound,
b) contacting, in vitro, said cancer cells with said culture medium to produce first contacted cells,
c) contacting said first contacted cells with said test compound to produce second contacted cells,
d) measuring wild type IDH1 enzyme activity in said second contacted cells, wherein reduced wild type IDH1 enzyme activity in said second contacted cells compared to said first contacted cells identifies said test compound as having anti-cancer activity.

In one embodiment, said culture medium comprises magnesium$^{2+}$ ($Mg^{2\pm}$) at a concentration lower than 0.5 mM.

BRIEF DESCRIPTION OF THE DRAWINGS

FIG. 1A. Wild type IDH1 activity: FIG. 1A) Wild type IDH1 typically proceeds to the right under metabolic stress (oxidative decarboxylation producing α-ketoglutarate), and to the left under normal (absence of disease) conditions (reductive carboxylation producing isocitrate). FIG. 1B) Mutant IDH1 produces D-2-hydroxyglutarate (2-HG) and consumes NADPH.

FIG. 2A-C. IDH1 knockout in pancreatic cell line MiaPaCa2 cells. FIG. 2A) Crystal violet clonogenic assay reveals decreased growth under low glucose (2.5 mM) and rescue by N-aceyticysteine (1.25 mM). FIG. 2B) DNA quantitation; wtIDH1 rescued IDH1−/− cells from gemcitabine under glucose withdrawal while mutant IDH1 did not. FIG. 2C) Impaired IDH1−/− xenograft growth.

FIG. 3 A-B. AG-120 is a potent inhibitor of wtIDH1 activity in an in vitro cell-free assay under low magnesium ion conditions, but not under typical cell culture conditions where magnesium levels are similar to serum conditions. FIG. 3A) In an ex vitro enzyme activity assay, AG-120 has poor activity under standard cell culture conditions containing 1 mM $Mg^{2+}$, but FIG. 3B) is extremely potent as a wild type IDH1 inhibitor when $Mg^{2+}$ is lowered to levels present in the tumor microenvironment, such as 0.3 mM (almost 1000-fold lower IC50).

FIG. 8(A) AG-120, FIG. 8(B) AGI-5198, FIG. 8(C) Agios 135, FIG. 8(D) ML309, FIG. 8(E) Novartis 224, FIG. 8(F) Novartis 556, FIG. 8(G) Novartis 533, FIG. 8(H) GSK864, FIG. 8(I) Sanofi 1, FIG. 8(J) AGI-6780, FIG. 8(K) AG-221, and FIG. 8(L) IDH2-C100, and described in Lin et al. (2019) J. Medicinal Chem 62: 6575-6596 and Ma et al. (2018) J. Medicinal Chem. 61: 8981-9003 FIG. 8(M) GSK321, FIG. 8(N) BAY-1436032, FIG. 8(O) IDH305, and FIG. 8(P) DS1001.

FIG. 9A-E: Mutant IDH inhibitors described in FIG. 9(A) U.S. Pat. No. 9,968,595 and U.S. Patent publication 20170014396, FIG. 9(B) U.S. Pat. No. 9,662,327, FIG. 9(C) U.S. Pat. No. 9,850,277 and U.S. Patent publication 20190046512, FIG. 9(D) U.S. patent publication 20130190249, and FIG. 9(E) U.S. patent publication 20180353514.

FIG. 10. Human wild type IDH1 amino acid sequence (SEQ ID NO:01) listed at GenBank NCBI Reference Sequence: NM_005896.3.

FIG. 11. Commercial mutant IDH1 inhibitors show significant inhibition of wild type IDH1 isozyme in low magnesium (0.08 mM) in pancreas cell based assay. AG-120 was used at 100 nM.

FIG. 12. AG-120 (1 μM) is lethal to pancreatic cancer cells under low nutrient conditions, including low $Mg^{2+}$ level of 0.08 mM and low glucose level of 2.5 mM.

FIG. 13. At high temperatures and low Mg2+ level of 0.08 mM, AG-120 (1 μM) stabilizes wild type IDH1 in pancreatic cells.

FIG. 14. AG-120 is effective as a monotherapy in colon cancer expressing wild type IDH1.

FIG. 15. AG-120 inhibits H460 large cell lung adenocarcinoma xenografts expressing wild type IDH1.

FIG. 16. AG-120 inhibits TS603 glioma cell line with IDH1 mutation.

FIG. 18B) Sugar-water consumption increased intra-tumoral glucose levels greater than 3-fold.

DEFINITIONS

Figure 4:
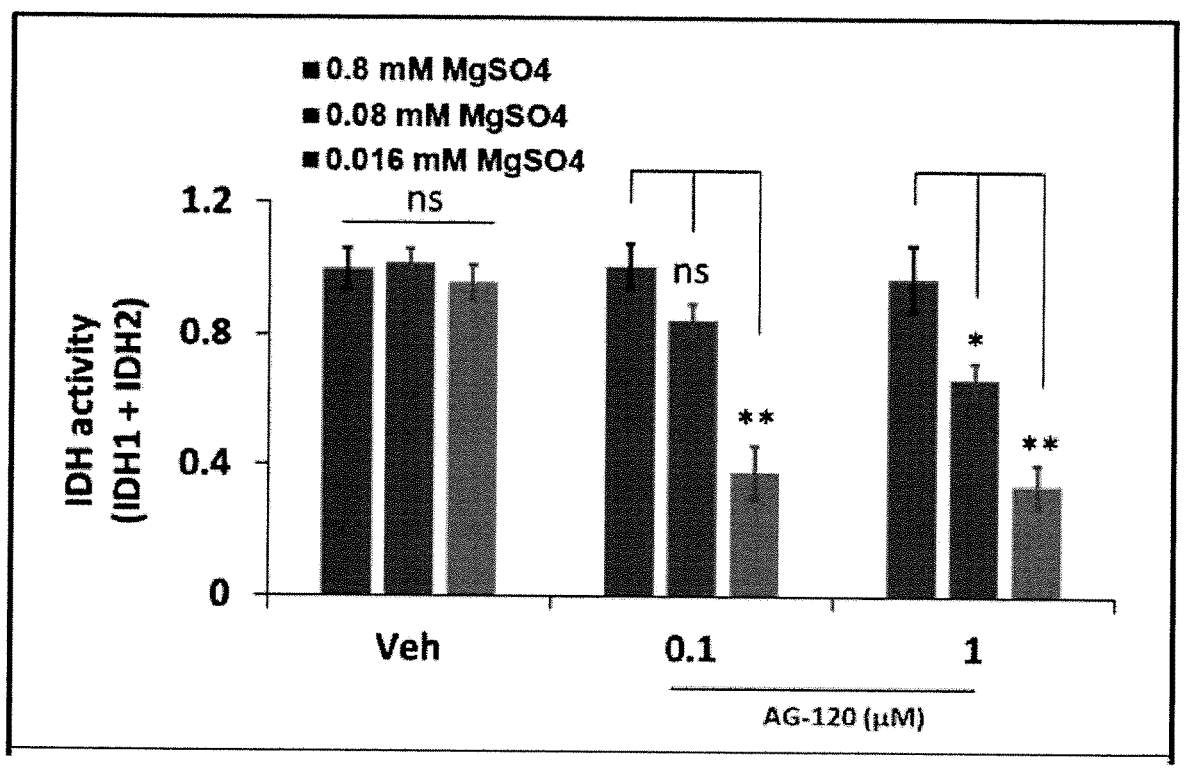
FIG. 4. AG-120 (1 μM) inhibits wtIDH1 enzyme activity in an in vitro cell-based assay under low magnesium ion concentrations. A cell-based IDH activity assay showed pre-culture of pancreatic cancer cell line (MiaPaCa2) with relatively low Mg levels sensitizes cells to AG-120 to wild type IDH1 inhibition (purple and green bars, compared to red). Cells were pre-cultured with low MgS04 medium for 1.5 hours followed by 3 hours AG-120 treatment.

To facilitate understanding of the invention, a number of terms are defined below.

"Wild type isocitrate dehydrogenase 1," "wild type isocitrate dehydrogenase (NADP(+)) 1," "wild type IDH1," 'wtIDH1," and "WT IDH1," interchangeably refer to a cytosolic enzyme that interconverts isocitrate and α-ketoglutarate. The enzyme utilizes NADP(H) as a cofactor for the reaction (FIG. 1A-B). Under low nutrient conditions present in the tumor microenvironment, the reaction may favor the oxidative direction, and the production of NADPH (right direction in the figure). Methods for measuring wild type IDH1 enzyme activity are known in the art (Urban et al. 2017). In one embodiment, wild type IDH1 has an amino acid sequence exemplified by human SEQ ID NO:01 (FIG. 10) (NCBI Reference Sequence: NM_005896.3), which is characterized by having amino acid Arg at residue 132. The term wild type IDH1 is contemplated to include proteins having at least 95% homology with SEQ ID NO:01, and having the enzyme activity shown in panel A of FIG. 1 A-B.

"Wild type isocitrate dehydrogenase (NADP(+)) 1," "wild type isocitrate dehydrogenase 1," and "WT IDH1" when in reference to a gene interchangeably refer to a DNA sequence encoding wild type IDH1 enzyme.

"Mutant isocitrate dehydrogenase 1," "mutant IDH1," and "mIDH1" when in reference to an enzyme interchangeably refer to an IDH1 enzyme containing a mutation (i.e., addition and/or deletion and/or substitution) relative to the wild type IDH1 enzyme. IDH1 mutations at the arginine 132 residue divert α-ketoglutarate to an oncometabolite, 2-hydroxyglutarate (2-HG) (FIG. 1B). This reaction may be deleterious under low nutrient conditions in the tumor because it consumes NADPH to regenerate NADP+.[1,2] As a result, the tumor may be more susceptible to oxidative damage since NADPH provides reducing power to cells through the donation of electrons to antioxidant defense pathways. Methods for measuring mutant IDH1 activity are known in the art (Urban et al. 2017). In one embodiment the mutant IDH1 enzyme has an R132X mutation, i.e., has an amino acid other than an Arg at residue 132 of the protein sequence SEQ ID NO:01 (FIG. 10). Thus, in one aspect of this embodiment, the R132X mutation is selected from R132H, R132C, R132L, R132V, R132S and R132G.

"Mutant isocitrate dehydrogenase 1," "mutant IDH1," and "mIDH1" when in reference to a gene interchangeably refer to a gene encoding a mutant IDH1 enzyme.

The term cell "characterized by the presence of wild type isocitrate dehydrogenase 1 (IDH1) gene" means a cell having a genome that contains two copies of wild type isocitrate dehydrogenase 1 (IDH1) DNA, and that lacks copies of mutant isocitrate dehydrogenase 1 (IDH1) DNA. The term cell "characterized by the presence of wild type IDH1 enzyme" means a cell that expresses only wild type IDH1 enzyme and that does not express mutant IDH1 enzyme. It is optional, but not necessary, for the invention's methods to detect wild type IDH1 gene and/or wild type IDH1 mRNA and/or wild type IDH1 enzyme (e.g., by sequencing the cells' IDH1 DNA and/or sequencing the cells' IDH1 mRNA and/or measuring the enzyme activity of the cell's IDH1 enzyme).

The terms "detecting wild type IDH1 gene" and "detecting wild type IDH1 enzyme" interchangeably refer to direct or indirect detection of wild type IDH1 gene and/or of wild type IDH1 enzyme, such as by measuring IDH1 enzyme activity and/or sequencing IDH1 mRNA and/or sequencing IDH1 genomic sequence to determine the presence of only wild type IDH1 enzyme and/or wild type IDH1 mRNA and/or wild type IDH1 genomic sequence. In another embodiment, the term "detecting wild type IDH1 gene" also refers to measuring IDH1 enzyme activity and/or sequencing IDH1 mRNA and/or sequencing IDH1 genomic sequence to determine the absence of mutant type IDH1 enzyme and/or mutant IDH1 mRNA and/or mutant IDH1 genomic sequence. The optional detecting step may carried out before and/or after administering to the subject one or more compounds that inhibit mutant IDH1 enzyme.

Figure 8A:
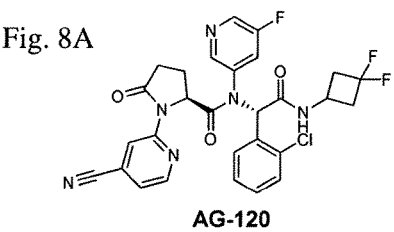
FIG. 8A-P. Mutant IDH inhibitors described in Urban et al. (2017) Sci Rep, vol 7:12758, pages 1-15.
Figure 8B:
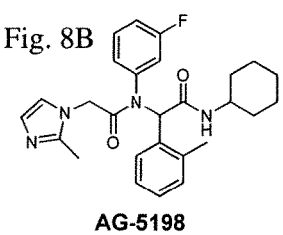
Figure 8C:
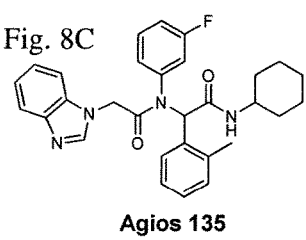
Figure 8D:
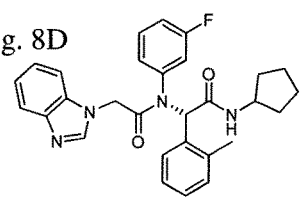
Figure 8E:
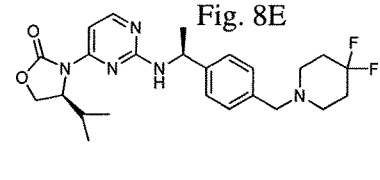
Figure 8F:
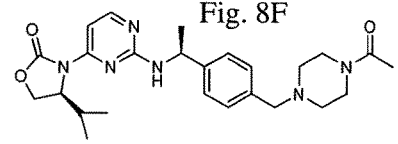
Figure 8G:
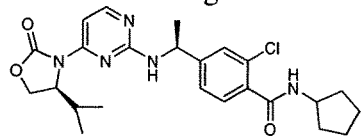
Figure 8H:
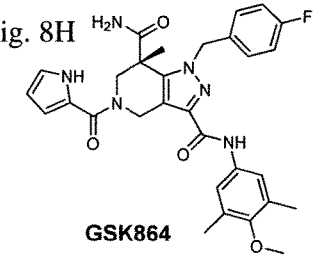
Figure 8I:
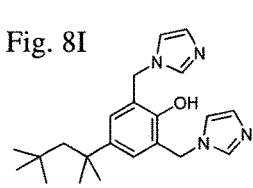
Figure 8J:
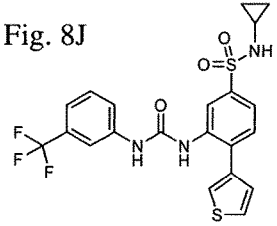
Figure 8K:
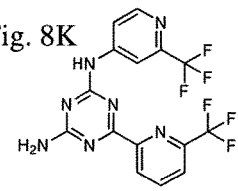
Figure 8L:
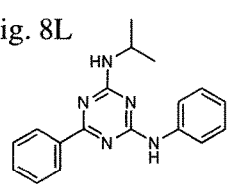
Figure 8M:
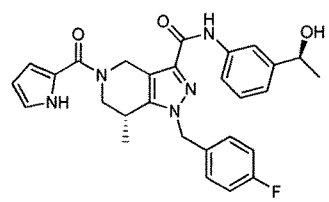
Figure 8N:
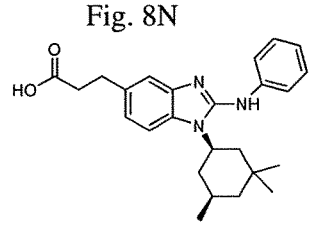
Figure 8O:
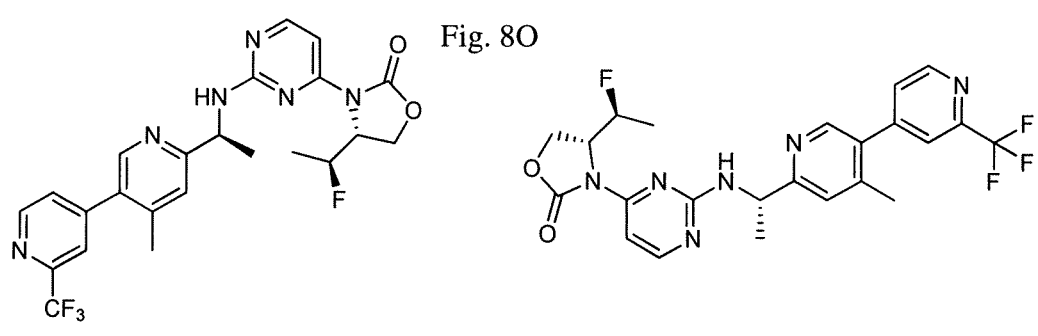
Figure 8P:
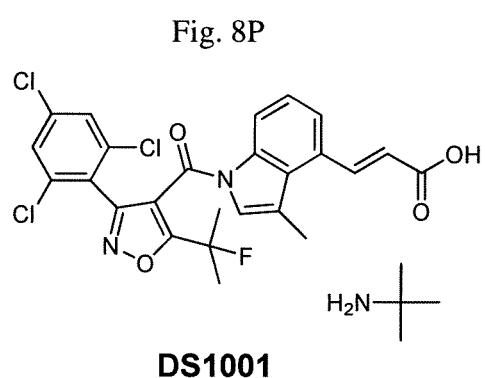

"Ivosidenib" and "AG-120" interchangeably refer to a compound having the Formula $C_{28}H_{22}ClF_3N_6O_3$ as depicted in FIG. 8A, and is available from Agios Pharmaceuticals, Inc. AG-120 is an inhibitor of mutant IDH1.[3] It was developed with intended selectivity for the mutant IDH1 over wild type IDH1.[3] AG-120 was approved by the FDA for acute myeloid leukemia (AML) with an IDH1 mutation and is presently in a phase III clinical trial for cholangiocarcinoma with an IDH1 mutation (Clinical trial number NCT03173248).

"Overexpression," "upregulation," and grammatical equivalents, when used in reference to a protein (such as a wild type IDH1 enzyme, mutant IDH1 enzyme, etc.) in a cell of interest refer to the presence of a higher level of the protein and/or its encoding mRNA, in the cell of interest (such as a cancerous cell) compared to another cell (such as a control non-cancerous cell).

"Underexpression," "downregulation," and grammatical equivalents, when used in reference to a protein (such as a wild type IDH1 enzyme, mutant IDH1 enzyme, etc.) in a cell of interest refers to the presence of a lower level of the protein and/or its encoding mRNA, in the cell of interest (such as a cancerous cell) compared to another cell (such as a control non-cancerous cell).

"Cancer" refers to a plurality of cells undergoing early, intermediate or advanced stages of multi-step neoplastic progression. Cancer may be a primary cancer, recurrent cancer, and/or metastatic cancer. The place where a cancer starts in the body is called the "primary cancer" or "primary site." If cancer cells spread to another part of the body the new area of cancer is called a "secondary cancer" or a "metastasis." "Recurrent cancer" means the presence of cancer after treatment and after a period of time during which the cancer cannot be detected. The same cancer may be detected at the primary site or somewhere else in the body, e.g., as a metastasis. "Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates. Cancer is exemplified by pancreatic cancer, ovarian cancer, breast cancer, lung cancer, prostate cancer, cervical cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), bile duct cancer, small intestine cancer, and soft tissue sarcomas.

"Cell line" and "immortalized cells" refer to cells capable of a greater number of cell divisions in vitro before cessation of proliferation and/or senescence as compared to a primary cell from the same tissue source. "Cancer cell line" refers to a cell line derived from primary cancer tissue. Cancer cell lines are commercially available, such as from ATCC. In one embodiment, the cancer cell line is exemplified by pancreatic cell line MiaPaCa2, pancreatic cell line Panc1, colon cancer cell line HCT116, large cell lung carcinoma cell line H460.

A "primary cancer cell" is a cell that is obtained directly from a cancer tissue of an animal whether or not the cell is in culture.

"Treating" a disease and "reducing" a disease (e.g., cancer) refers to delaying, reducing, palliating, ameliorating, stabilizing, preventing and/or reversing one or more symptoms (such as objective, subjective, pathological, clinical, sub-clinical, etc.) of the disease. In the case of cancer, objective symptoms are exemplified by tumor size (e.g. dimensions, weight and/or volume), tumor number, rate of change in tumor size and/or number, presence of metastasis, metastasis size (e.g. dimensions, weight and/or volume), metastasis number, and/or rate of change in metastasis size and/or number. Subjective symptoms are exemplified by pain, fatigue, etc. Cancer symptoms may be assessed by, for example, biopsy and histology, and blood tests to determine relevant enzyme levels or circulating antigen or antibody, and imaging tests which can be used to detect a decrease in the growth rate or size of a neoplasm.

"Pharmaceutical" and "physiologically tolerable" composition interchangeably refer to a composition that contains molecules that are capable of administration to or upon a subject and that preferably do not substantially produce an undesirable effect such as, for example, adverse or allergic reactions, dizziness, gastric upset, toxicity and the like, when administered to a subject. Preferably also, molecules in the pharmaceutical composition do not substantially reduce the activity of active ingredient in the compositions. Pharmaceutical molecules include "diluent" (i.e., "carrier") molecules and excipients. "Diluents" include water, saline solution, human serum albumin, oils, polyethylene glycols, aqueous dextrose, glycerin, propylene glycol or other synthetic solvents. "Carriers" may be liquid carriers (such as water, saline, culture medium, saline, aqueous dextrose, and glycols) or solid carriers (such as carbohydrates exemplified by starch, glucose, lactose, sucrose, and dextrans, antioxidants exemplified by ascorbic acid and glutathione, and hydrolyzed proteins).

"Therapeutic amount," "pharmaceutically effective amount," and "therapeutically effective amount," are used interchangeably herein to refer to an amount that is sufficient, upon single or multiple dose administration, to achieve a desired result, such as treating disease and/or reducing activity of an enzyme (e.g., wild type IDH1) associated with disease beyond that expected in the absence of such administration.

"IC50" and "half maximal inhibitory concentration" interchangeably refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an inhibitor's potency.

"Mammalian subject" includes human, non-human primate, murine (e.g., mouse, rat, guinea pig, hamster, ovine, bovine, ruminant, lagomorph, porcine, caprine, equine, canine, feline, ave, etc.).

A subject "in need" of treatment with the invention's methods includes a subject "suffering from disease," i.e., a subject experiencing and/or exhibiting one or more symptoms of the disease, and subject "at risk" of the disease. A subject "in need" of treatment includes animal models of the disease. Subject "at risk" of disease refers to a subject not currently exhibiting disease symptoms and is predisposed to expressing one or more symptoms of the disease. This predisposition may be genetic based on family history, genetic factors, environmental factors such as exposure to detrimental compounds present in the environment, etc.). It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The term "administering" a composition to a subject means delivering the composition to the subject, including prophylactic administration of the composition (i.e., before the disease and/or one or more symptoms of the disease are detectable) and/or therapeutic administration of the composition (i.e., after the disease and/or one or more symptoms of the disease are detectable). The invention's methods include administering a combination of a first composition (e.g., wild type IDH1 inhibitor and/or mutant IDH1 inhibitor) and a second composition (e.g., chemotherapeutic drug). In one embodiment, the first and second compositions may be mixed together prior to administration. In another embodiment, the first and second compositions may be administered simultaneously at substantially the same time, and/or administered sequentially at different times in any order (first composition followed second composition, or second composition followed by first composition). For example, administering the second composition substantially simultaneously and sequentially in any order includes, for example, (a) administering the first and second compositions simultaneously at substantially the same time, followed by administering the first composition then the second composition at different times, (b) administering the first and second compositions simultaneously at substantially the same time, followed by administering the second composition then the first composition at different times, (c) administering the first composition then the second composition at different times, followed by administering the first and second compositions simultaneously at substantially the same time, and (d) administering the second composition then the first composition at different times, followed by administering the first and second compositions simultaneously at substantially the same time.

Administering may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the compositions may be administered before, concomitantly with, and/or after administration of another type of drug or therapeutic procedure (e.g., surgery). Methods of administering the compositions include, without limitation, administration in parenteral, oral, intraperitoneal, intranasal, topical and sublingual forms. Parenteral routes of administration include, for example, subcutaneous, intravenous, intramuscular, intrastemal injection, and infusion routes.

The terms "reduce," "inhibit," "diminish," "suppress," "decrease," and grammatical equivalents when in reference to the level of any molecule (e.g., magnesium ion, glucose, amino acid sequence, nucleic acid sequence, etc.), cell (e.g., cancer cell), and/or phenomenon (e.g., disease symptom, enzyme activity such as IDH1 enzyme activity), in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis.

The terms "increase," "elevate," "raise," "higher," "greater," and grammatical equivalents when in reference to the level of any molecule (e.g., magnesium ion, glucose, amino acid sequence, nucleic acid sequence, etc.), cell (e.g., cancer cell), and/or phenomenon (e.g., disease symptom, enzyme activity such as IDH1 enzyme activity, expression levels such as IDH1 protein expression), in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

DESCRIPTION OF THE INVENTION

The invention provides methods of treating cancer characterized by the presence of one or both of wild type isocitrate dehydrogenase 1 (IDH1) gene and wild type IDH1 enzyme, by administering compounds that inhibit mutant IDH1 enzyme, such as Ivosidenib (AG-120, IVO-SIDENIB®). The invention also provides cell-based methods for determining anti-cancer activity of test compounds under in vitro conditions of low concentrations of magnesium ion and/or glucose.

Figure 18A:
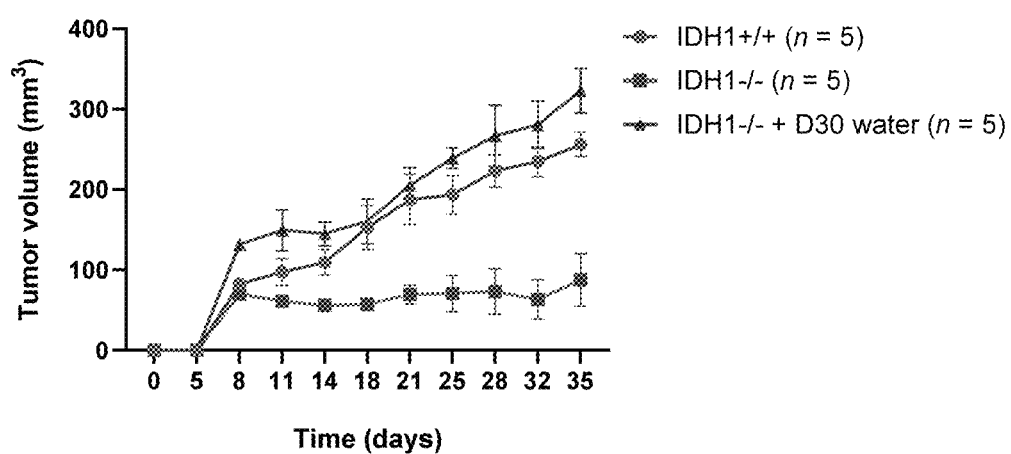
FIG. 18A-B. Raising serum and intra-tumoral glucose levels in mice through consumption of sugar-water FIG. 18A) rescued IDH1-knockout pancreatic cancer cell growth.
Figure 18B:
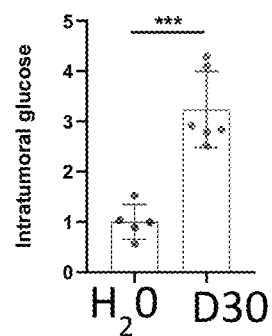
Figure 19:
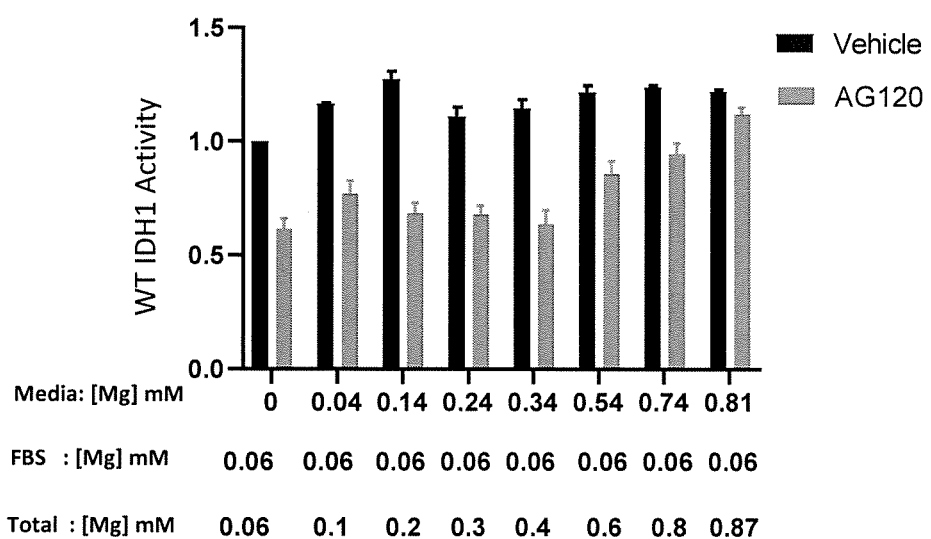
FIG. 19. AG-120 (1 µM) is not inhibitory of wild type IDH1 enzyme activity at physiologic serum Mg2+ concentrations, but reduces wild type IDH1 enzyme activity by 50% below 0.4 mM (simulates the tumor microenvironment).
Figure 20:
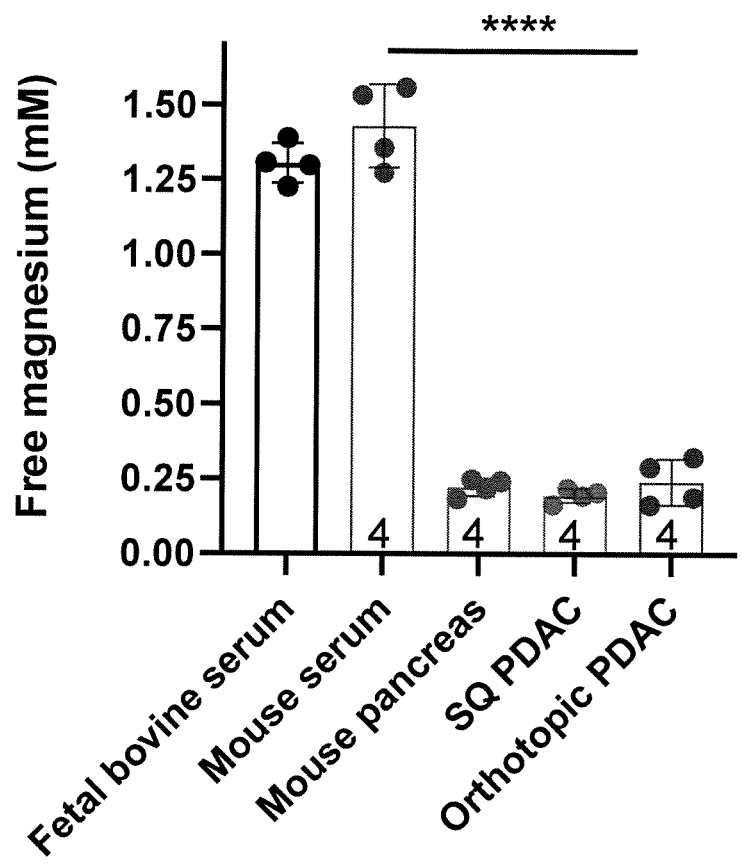
FIG. 20. SQ and orthotopic pancreatic tumors have Mg2+ levels sufficiently low for ivosidenib to be effective (below 0.4 mM). While normal tissues do as well, only cancers have both low Mg2+ (drug active) and low glucose (IDH1 important).

The invention's methods were based on the surprising discovery that inhibitors of mutant IDH1 were also effective in inhibiting wild type IDH1 only when assayed in vitro under low magnesium ion concentrations (whether or not low glucose concentrations were also present). Several drugs (e.g., AG-120) have been developed in the prior art to inhibit cancer by selectively inhibiting mutant IDH1 over wild type IDH1.[3,4] The concept behind the development of drugs that inhibit cancer by selectively targeting the mutant IDH1 is that normal cells express the wild type form of IDH1, and this selectivity for the mutant IDH1 spares normal cells from the drug's side effects. In fact, the prior art shows 100-fold potency of AG-120 for the mutant IDH1 compared to the wild type IDH1 under standard culture conditions.[4] Also, the prior art shows that the wild type IDH1 isoenzyme should not be as sensitive as the mutant IDH1 isoenzyme to low magnesium ion effects because the Km is nearly 300-fold lower.[5] Prior literature suggests the Km value for $Mg^{2+}$ is 20 μM. These were cell free studies (Dent et al. JBC 2015. volume 290 (2); 762-774), and suggest that magnesium concentrations below 0.5 mM and above 20 μM would previously not be presumed to have a strong biologic affect on wild type IDH1 activity. Data herein demonstrate, surprisingly and for the first time, that these small drug compounds that inhibit mutant IDH1 also potently block wild type IDH1, but only when assayed in vitro under low magnesium ion concentrations, and the effect is seen in cancer cells below 0.5 mM $Mg^{2+}$ (FIG. 4, FIG. 6, FIG. 11, and FIG. 19). This discovery has important implications for both screening test cancer drugs for their ability to inhibit wild type IDH1, and using inhibitors of mutant IDH1 to treat cancers expressing wild type IDH1 since tumors often have low magnesium ion concentration (FIG. 20). Normal non-cancer tissues may have higher magnesium concentrations where these inhibitors would not effectively inhibit the wild type isoenzyme (Seltzer et al., Serum and tissue magnesium levels in human breast carcinoma, J Surg Res, 1970. 10(4): p. 159-62; Fuhrmann et al., Metastatic State of Cancer Cells May Be Indicated by Adhesion Strength. Biophys J, 2017. 112(4): p. 736-745). While low magnesium levels allow the drug to be a more active inhibitor, inhibition of wild type IDH1 is biologically important for cell viability when nutrients and oxidative stress is high. Therefore, IDH1 inhibition through genetic modulation or pharmacologically results in increase cell death and increase oxidative stress under low glucose conditions (or chemotherapy stress), but not high glucose conditions (FIGS. 2A, 2B, FIG. 5, FIG. 6, FIG. 12, FIG. 18A-B). Tumors have both conditions for IDH1 inhibition using mutant IDH1 inhibitors; 1) low magnesium renders the drugs active as inhibitors; 2) low nutrients or other oxidative stress renders IDH1 important for cancer cell survival. Low glucose levels in tumors is a well established phenomenon in pancreatic and other cancers (Zeibert et al. J Cancer Res Clin Oncol (2011) 137: 193-199; Kamphorst et al., Cancer Res; 75 (3); 544-53).

The invention is further described under (A) Assays of candidate drugs for treatment of wild type IDH1 cancers, and (B) Methods of treating wild type IDH1 cancer.

(A) Assays of Candidate Drugs for Treatment of Wild Type IDH1 Cancers

The invention provides cell-based methods for determining anti-cancer activity of test compounds under in vitro conditions of low concentrations of magnesium ion and/or glucose. In one embodiment, the invention provides a method for determining anti-cancer activity of a test compound, comprising
   a) providing
      i) cancer cells (e.g., cancer cell line cells, or primary cancer cells) characterized by the presence of one or both of wild type isocitrate dehydrogenase 1 (IDH1) gene and wild type IDH1 enzyme,
      ii) culture medium comprising magnesium$^{2+}$ (Mg$^{2+}$) at a concentration lower than 0.5 mM, and
      iii) the test compound,
   b) contacting, in vitro, the cancer cells with the culture medium to produce first contacted cells,
   c) contacting the first contacted cells with the test compound to produce second contacted cells,
   d) measuring wild type IDH1 enzyme activity in the second contacted cells, wherein reduced wild type IDH1 enzyme activity in the second contacted cells compared to the first contacted cells identifies the test compound as having anti-cancer activity.

Magnesium ion (Mg$^{2+}$) concentrations are 0.5-1 mM in the serum of patients, and Mg$^{2+}$ concentrations fall in this range in standard tissue culture media (e.g., DMEM). However, concentrations are nearly an order of magnitude less in the tumor microenvironment (approximately 0.1 to 0.3 mM).

Data herein also show the surprising discovery of a 3-fold increase in reactive oxygen species (ROS) with 1 μM AG-120 treatment under low Mg$^{2+}$ concentration (zero mM Mg$^{2+}$) and low glucose concentration (2.5 mM glucose).

Thus, in one embodiment, the invention's in vitro assays employ Mg$^{2+}$ at concentrations lower than 0.5 mM, i.e., lower than those in the serum of patients and lower than those in standard tissue culture media. Exemplary Mg$^{2+}$ concentrations "lower than 0.5 mM" include, without limitation, from 0 to 4.9, 0 to 4.8, 0 to 4.7, 0 to 4.6, 0 to 4.5, 0 to 4.4, 0 to 4.3, 0 to 4.2, 0 to 4.1, 0 to 4.0, 0 to 3.9, 0 to 3.8, 0 to 3.7, 0 to 3.6, 0 to 3.5, 0 to 3.4, 0 to 3.3, 0 to 3.2, 0 to 3.1, 0 to 3.0, 0 to 2.9, 0 to 2.8, 0 to 2.7, 0 to 2.6, 0 to 2.5, 0 to 2.4, 0 to 2.3, 0 to 2.2, 0 to 2.1, 0 to 2.0, 0 to 1.9, 0 to 1.8, 0 to 1.7, 0 to 1.6, 0 to 1.5, Oto 1.4, 0 to 1.3, 0 to 1.2, 0 to 1.1, 0 to 1.0, 0 to 0.9, 0 to 0.8, 0 to 0.7, 0 to 0.6, 0 to 0.5, 0 to 0.4, 0 to 0.3, 0 to 0.2, 0 to 0.1, 0 to 0.09, 0 to 0.08, 0 to 0.07, 0 to 0.06, 0 to 0.05, 0 to 0.04, 0 to 0.03, 0 to 0.02, 0 to 0.01, 0 to 0.09, 0 to 0.08, 0 to 0.07, 0 to 0.06, 0 to 0.05, 0 to 0.04, 0 to 0.03, 0 to 0.02, 0 to 0.01, 0 to 0.009, 0 to 0.008, 0 to 0.007, 0 to 0.006, 0 to 0.005, 0 to 0.004, 0 to 0.003, 0 to 0.002, and 0 to 0.001 mM. In one embodiment, Mg$^{2+}$ concentration is 0.3 mM (Example 2, FIG. 3A-B), 0.08 mM, and 0.016 mM (Example 3, FIG. 4). In another embodiment, Mg$^{2+}$ is absent (i.e., Mg$^{2+}$ concentration is zero) (Example 5, FIG. 6). Exemplary low Mg$^{2+}$ levels are shown in FIGS. 4, 6, 11, 12, 13, 19 and 20.

Figure 5:
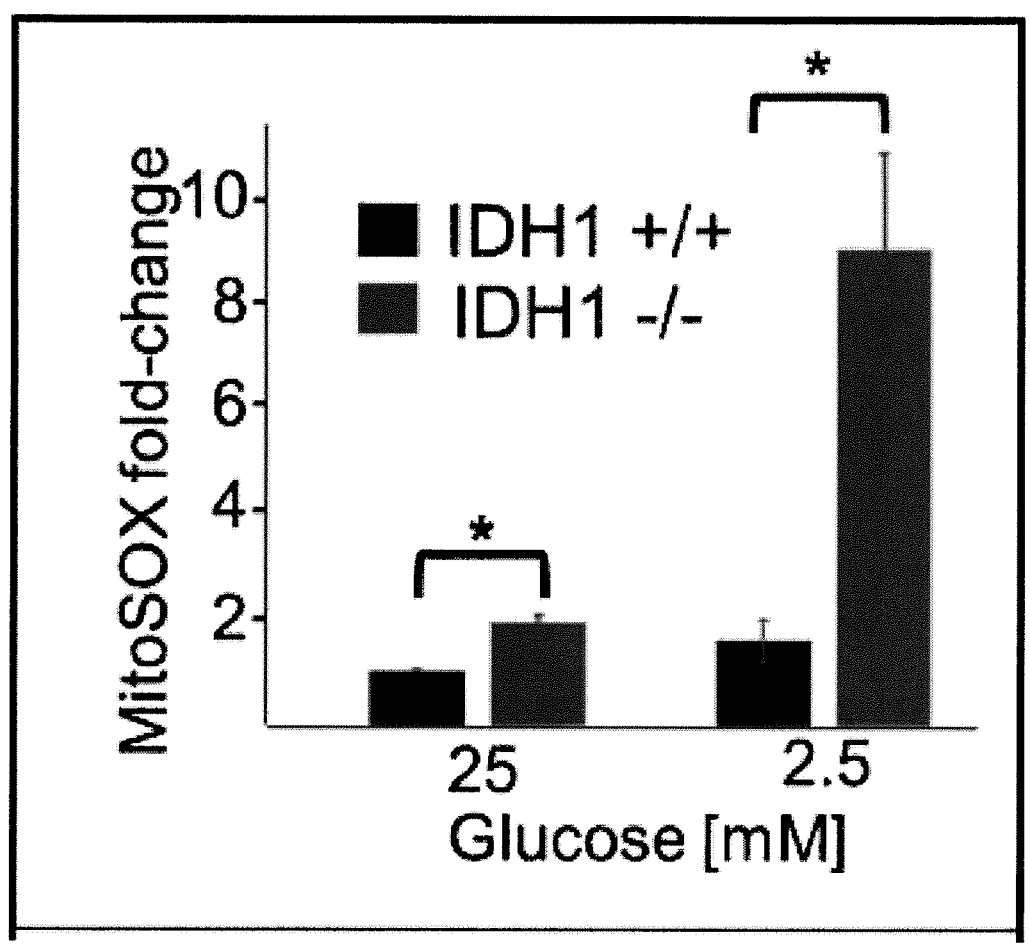
FIG. 5. Reactive oxygen species (ROS) levels are increased in IDH1-knockout cells under low glucose concentrations (2.5 mM) showing the importance of IDH1 under low nutrient conditions present in tumors.
Figure 6:
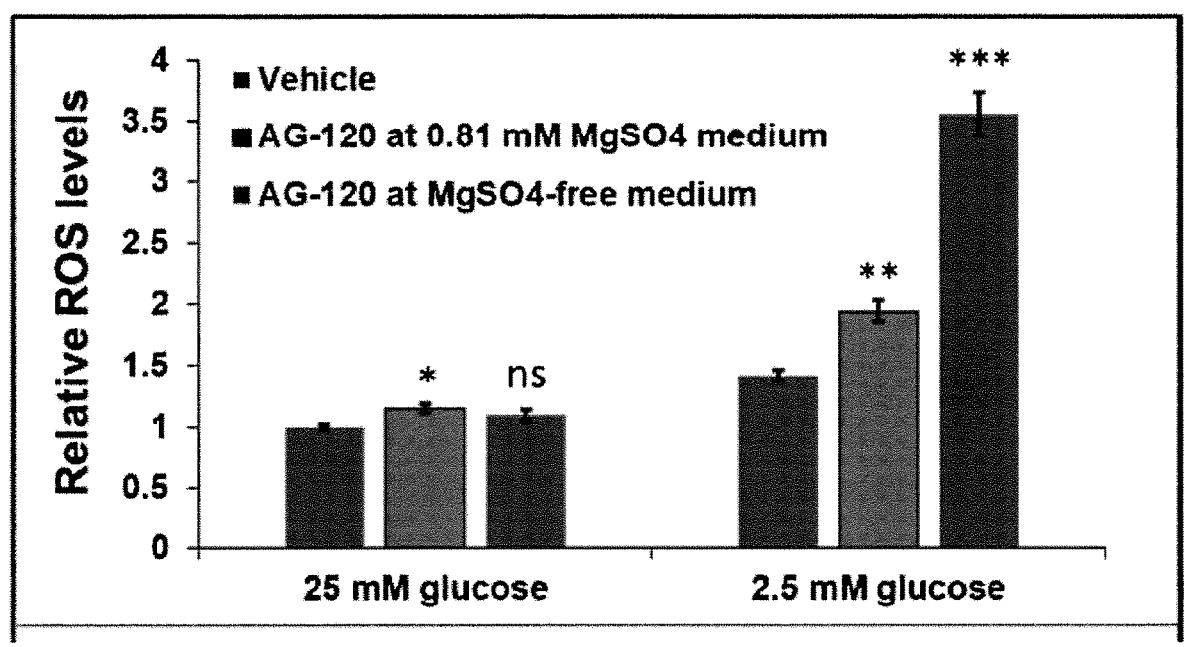
FIG. 6. AG-120 (1 μM) induces ROS in an in vitro cancer cell-based assay only under conditions with low Mg and low glucose (2.5 mM). Pancreatic cancer cell line (Panel) cells were treated with AG-120 (1 μM) under different levels of $MgSO_4$ and glucose for 48 hours.

In one embodiment, the culture medium further comprises glucose at a concentration lower than 25 mM (Example 4, FIG. 5; and Example 5, FIG. 6). Exemplary glucose concentrations "lower than 25 mM" include, without limitation, from 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, 1 to 1.9, 1 to 1.8, 1 to 1.7, 1 to 1.6, 1 to 1.5, 1 to 1.4, 1 to 1.3, 1 to 1.2, and 1 to 1.1 mM. In one embodiment, glucose concentration is 2.5 mM (Example 4, FIG. 5; and Example 5, FIG. 6). Exemplary low glucose levels of 2.5 mM are used in FIGS. 2A, 5, 6 and 12.

While not intending to limit the order in which the invention's steps are carried out, in one embodiment, the contacting of step b) is before the contacting of step c) (Example 4, FIG. 5; and Example 5, FIG. 6). In another embodiment, the contacting of steps b) and c) is simultaneous.

It is not intended that the invention be limited to the type of test compound assayed using the invention's methods. However, in one embodiment, the test compound inhibits mutant IDH1 enzyme activity and/or wild type IDH1 enzyme activity, as exemplified by one or more of the compounds listed in FIG. 8A-P and FIG. 9A-E. In a particular embodiment, the compound comprises AG-120 (FIG. 8A) (Example 6).

The invention also provides a method for determining anti-cancer activity of a test compound, comprising
   a) providing
      i) cancer cells characterized by the presence of one or both of wild type isocitrate dehydrogenase 1 (IDH1) gene and wild type IDH1 enzyme,
      ii) culture medium comprising glucose at a concentration lower than 25 mM, and
      iii) the test compound,
   b) contacting, in vitro, the cancer cells with the culture medium to produce first contacted cells,
   c) contacting the first contacted cells with the test compound to produce second contacted cells,
   d) measuring wild type IDH1 enzyme activity in the second contacted cells, wherein reduced wild type IDH1 enzyme activity in the second contacted cells compared to the first contacted cells identifies the test compound as having anti-cancer activity.

In one embodiment, the culture medium further comprises magnesium at a concentration "lower than 0.5 mM" (Example 2, FIG. 3A-B; Example 3; FIG. 4; and Example 5, FIG. 6). While not intending to limit the order in which the invention's steps are carried out, in one embodiment, the contacting of step b) is before the contacting of step c). In another embodiment, the contacting of steps b) and c) is simultaneous.

(B) Methods of Treating Wild Type IDH1 Cancer.

In one embodiment, the invention provides a method of treating cancer in a mammalian subject in need thereof, wherein the cancer contains cancer cells characterized by the presence of one or both of wild type isocitrate dehydrogenase 1 (IDH1) gene and wild type IDH1 enzyme, the method comprising the step of administering to the subject a pharmaceutical composition comprising a first compound that inhibits mutant IDH1 enzyme, wherein the pharmaceutical composition is in a therapeutic amount that reduces wild type IDH1 enzyme activity in the cancer cells. In one embodiment, the first compound that inhibits mutant IDH1 enzyme comprises one or more compounds listed in FIG. 8A-P and FIG. 9A-E. In a particular embodiment, the first compound comprises AG-120 (FIG. 8A) having the formula

Figure 7:
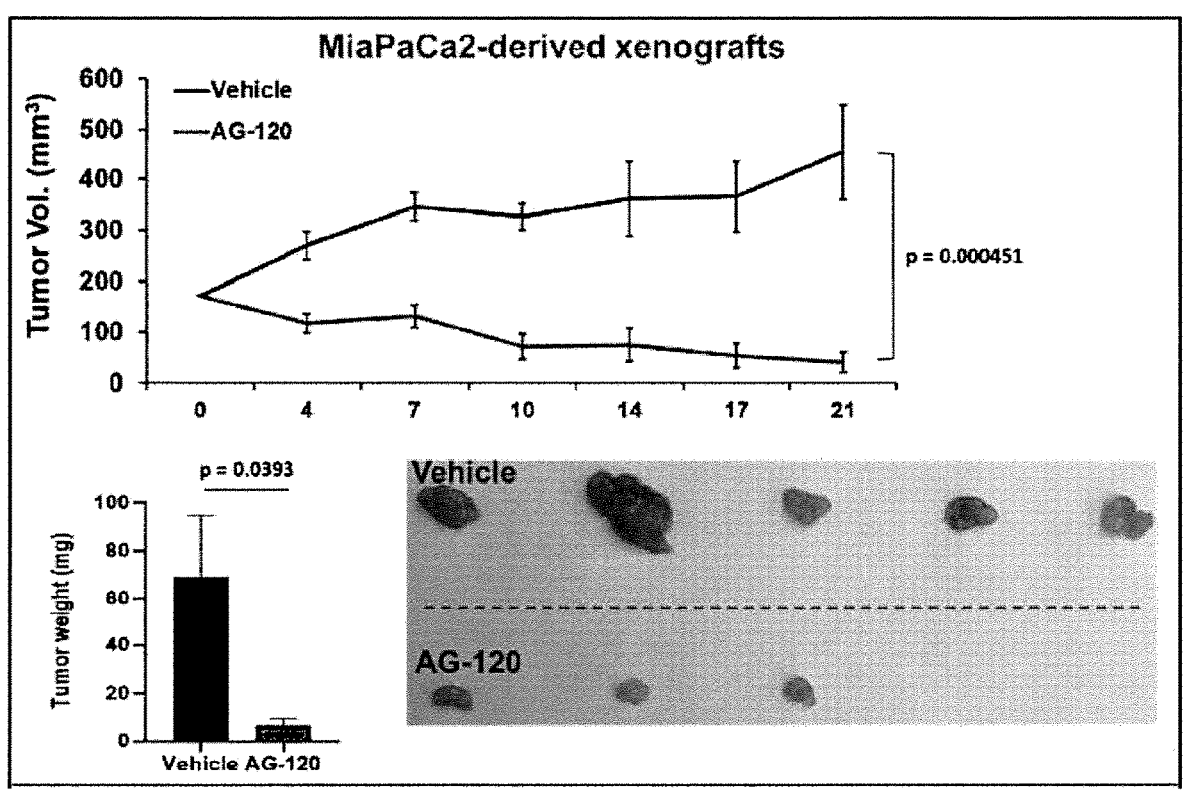
FIG. 7. AG-120 decreased tumor volume and tumor weight of pancreatic xenografts. Out of 5 xenografts per group, oral AG-120 was effective in reducing cancer in all cases, and completely cured the mice of cancer in 2 out 5 cases. No toxicity to mice occurred at these oral doses.
Figure 17:
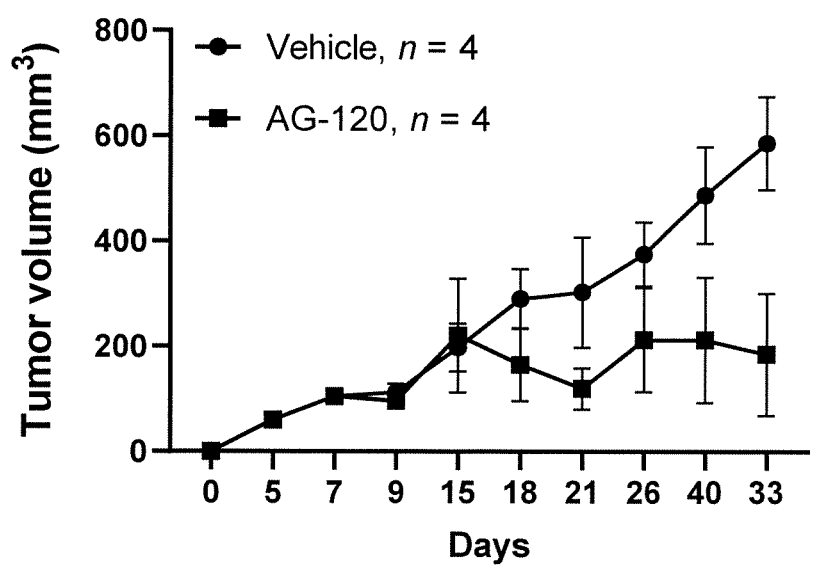
FIG. 17. Prior art drawing showing AG-120 inhibits A2700 human ovarian cancer xenografts expressing wild type IDH1.

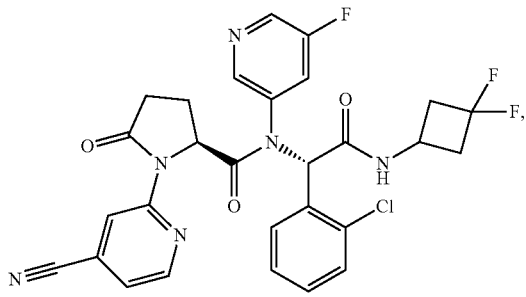

wherein the pharmaceutical composition is in a therapeutic amount that reduces wild type IDH1 enzyme activity in the cancer cells. Data herein demonstrate that AG-120 was remarkably potent against a wild type IDH1 human pancreatic cancer in an in vivo animal model (Example 6; FIG. 7), and against in vivo models of colon cancer (FIG. 14), lung cancer (FIG. 15) and ovarian cancer (FIG. 17).

While the efficacy of the invention's methods was demonstrated with respect to the exemplary pancreatic cancer (Example 6), it is expressly contemplated that the invention is not limited to any particular cancer so long as the cancer is characterized by the presence of one or both of wild type IDH1 enzyme (exemplified by amino acid sequence SEQ ID NO:01 (FIG. 10)), and wild type isocitrate dehydrogenase 1 (IDH1) gene encoding this enzyme.

While not intending to limit the level of expression of wild type IDH1 enzyme, in one embodiment, the wild type IDH1 enzyme is overexpressed in the cancer cells compared to non-cancerous cells of the same cell type (Zarei et al. 2017). In a further embodiment, the cancer cells are characterized by the absence of (i.e., the cancer cells lack) one or both of mutant IDH1 enzyme and of mutant IDH1 gene. In other words, the cancer cells need not have any copies of mutant IDH1 enzyme and/or of mutant IDH1 gene for the invention's methods to have efficacy. In particular embodiments, one or both of wild type IDH1 gene and wild type IDH1 enzyme is detected in a sample from the subject. While not intending to limit the type or source of sample, in one embodiment, the sample comprises one or both of tissue and "bodily fluid," including one or more of amniotic fluid surrounding a fetus, aqueous humor, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The invention's methods may further employ administering to the subject and anti-cancer compound, i.e., a second compound that reduces cancer, such a second compound used for chemotherapy and/or hormonal therapy and/or targeted therapy, as exemplified by 150 anticancer drugs approved by the US Food and Drug Administration (FDA) listed in Sun et al. BMC Systems Biology 2017, 11(Suppl 5):87 DOI 10.1186/s12918-017-0464-7.

It is not intended that the first compound be limited to any particular dosage. Thus, a therapeutic amount comprises from 15 to 1,500 mg/kg, including from 15 to 1,400, 15 to 1,300, 15 to 1,200, 15 to 1,100, 15 to 1,000, 15 to 900, 15 to 800, 15 to 700, 15 to 600, 15 to 500, 15 to 400, 15 to 300, 15 to 200, 15 to 100, 15 to 90, 15 to 80, 15 to 70, 15 to 60, 15 to 50, 15 to 40, 15 to 30, and 15 to 20 mg/kg. In a particular embodiment, data herein demonstrate successful anticancer activity of AG-120 in a therapeutic amount of 150 mg/kg in mice (Example 6, FIG. 7). In one embodiment, an equivalent therapeutic dose in a human subject is at 500 mg, which is approximately 7 mg/kg to treat IDH1 mutant AMPL. At 500 mg daily in humans, the exemplary AG-120 drug reaches plasma concentrations of 130 μM, which is about 2 orders of magnitude higher than the effect observed in culture (FIGS. 4, 6, 11, 12, 13, 19).

In one embodiment, the cancer treated in accordance with any of the invention's methods contains cancer cells having a lower Magnesium$^{2+}$ (Mg$^{2+}$) concentration compared to Mg$^{2+}$ concentration in serum, such as serum from the subject and/or serum from a control subject lacking cancer. Data herein in FIG. 20 show that the exemplary pancreatic cancer cells have low concentration of Mg$^{2+}$ (0.3 mM) compared to serum (1 mM). Data herein in FIG. 19 also show that AG-120 is not inhibitory of wild type IDH1 enzyme activity at physiologic serum Mg$^{2+}$ concentrations, but reduces wild type IDH1 enzyme activity by 50% below 0.4 mM.

In a further embodiment, the invention's methods further comprise reducing glucose concentration in blood of said subject. Data herein in FIG. 18A-B show that a high glucose diet adversely impacts the anti-cancer therapeutic effect of compounds that inhibit mutant IDH1 enzyme in cancers expressing wild type IDH1 enzyme. Similar adverse glucose effects were also observed in vitro. Thus, it may be desirable to treat cancer patients who have impaired glucose metabolism (see Table 1), i.e., who have impaired fasting glycaemia, impaired glucose tolerance, or diabetes mellitus by reducing their blood glucose concentrations before and/or during and/or after initiating treatment with one or more compounds that inhibits mutant IDH1 enzyme.

TABLE 1

WHO diabetes diagnostic criteria

| Condition | 2 hour glucose | | Fasting glucose | | HbA$_{1c}$ | |
|---|---|---|---|---|---|---|
| Unit | Mmol/L | Mg/dL | Mmol/L | Mg/dL | Mmol/mol | DCCT % |
| Normal | <7.8 | <140 | <6.1 | <110 | <42 | <6.0 |
| Impaired fasting glycaemia | <7.8 | <140 | 6.1-7.0 | 110-126 | 42-46 | 6.0-6.4 |
| Impaired glucose tolerance | ≥7.8 | ≥140 | <7.0 | <126 | 42-46 | 6.0-6.4 |
| Diabetes mellitus | ≥11.1 | ≥200 | ≥7.0 | ≥126 | ≥48 | ≥6.5 |

For example, in human patients, the blood glucose target range for diabetics, according to the American Diabetes Association, is 5.0-7.2 mmol/1(90-130 mg/dL) before meals, and less than 10 mmol/L (180 mg/dL) two hours after meals, as measured by a blood glucose monitor. Reduction in blood glucose levels may be achieved using methods known in the art, such as diet and/or physical exercise and/or medications such as insulin, vanadium-containing compounds, insulin sensitizers (exemplified by Biguanides, Thiazolidinediones and Lyn kinase activators), secretagogues that increase insulin output from the pancreas (exemplified by Sulfonylureas and Non-sulfonylurea secretagogues), alpha-glucosidase inhibitors that slow the digestion of starch in the small intestine, peptide analogs (exemplified by injectable incretin mimetics and injectable amylin analogues), and Glycosurics.

In a further embodiment, the method further comprises administering to the subject a compound that competes with glucose by acting as a D-glucose mimic, such as a non-metabolizable glucose analog, exemplified by 2-deoxyglucose (2DG) which impairs the cell's ability to utilize the glucose by inhibiting hexokinase/glycolysis. "Non-metabolizable" glucose analog refers to a derivative of glucose that is not metabolized by normal cells with access to oxygen via the process of glycolysis into two molecules of pyruvate to form two molecules of ATP. In a particular embodiment, the compound that competes with glucose enhances the anti-cancer activity of the compound that inhibits mutant IDH1, particularly in patients with high blood glucose where the compound that inhibits mutant IDH1 enzyme may not have significant anti-cancer activity.

EXPERIMENTAL

The following examples serve to illustrate certain preferred embodiments and aspects of the present invention and are not to be construed as limiting the scope thereof.

Example 1

Wild Type IDH1 (WT IDH1) Plays a Role in Pancreatic Cancer

Pancreatic cancer has low glucose (Kamphorst, cancer research 2015 75(3); 544-53). Cells of pancreatic cell line MiaPaCa2 containing wtIDH1 that was deleted using CRISPR/Cas9 gene editing had impaired survival under low glucose conditions (i.e., similar to the tumor microenvironment) in an in vitro experiment (FIG. 2A). IDH1-knockout cells failed to proliferate in mice, but when glucose levels were increased by diet, the IDH1-knockout cells proliferated. This indicates that IDH1 is important for pancreatic cancer cell survival when nutrients are low, but not when nutrients are abundant (FIG. 18A-B). This fact reveals that well nourished normal cells should suffer minimal toxicity from wild type inhibition. This is supported by the observation that wild type IDH1 whole body knockout mice do not exhibit an appreciable phenotype under baseline conditions (Itsumi, M., et al., IDH1 protects murine hepatocytes from endotoxin-induced oxidative stress by regulating the intracellular NADP(+)/NADPH ratio. Cell Death Differ, 2015. 22(11): p. 1837-45).

In MiaPaCa2 cells cultured under low glucose conditions and in the presence of gemcitabine chemotherapy, survival could be rescued by re-introducing the wild type IDH1 enzyme, but not by overexpressing the mutant IDH1 isoenzyme (FIG. 2B) illustrating the biologic importance of the wild type isoenzyme over the mutant isoenzyme. Additionally, wild type IDH1 knockout cells grow very poorly as xenografts (FIG. 2C).

This data show that WILD TYPE IDH1 is a promising target for treating pancreatic cancer.

Example 2

AG-120 is a Potent Inhibitor of wtIDH1 Activity in an In Vitro Cell-Free Assay Under Low Magnesium Ion Conditions A wild type IDH1 activity assay was performed under cell-free conditions, by co-incubating wild type IDH1, isocitrate, and NADP+. NADPH was measured, and the impact of AG-120 on the generation of the reduced molecule was determined.

Confirming previous reports, data herein showed that under standard culture conditions (1 mM magnesium ion), AG-120 had minimal potency in vitro because it is a poor wild type IDH1 inhibitor under these conditions (FIG. 3A).

Surprisingly, however, when we lowered the concentration to 0.3 mM in accordance with the invention's methods, AG-120 was highly potent as a wild type IDH1 inhibitor (FIG. 3B).

Surprisingly also, AG-120 had nearly 1000-fold potency as a wtIDH1 inhibitor when assayed under the low 0.3 mM magnesium ion culture concentration compared to the standard 1 mM magnesium ion culture concentration. Thus, AG-120 exhibited IC50 of 1.5 µM and 4 nM, respectively, when assayed under standard 1 mM magnesium ion culture concentration compared to the low 0.3 mM magnesium ion culture concentration.

The data demonstrate that AG-120 is a potent inhibitor of wtIDH1 activity in an in vitro cell-free assay under low magnesium ion conditions. Importantly, the data also demonstrate that the lowered AG-120 concentrations for reducing wtIDH1 activity under reduced magnesium ion concentrations that are observed in tumor cells are not toxic to cells outside the tumor microenvironment (e.g., normal cells) where magnesium ion levels may be higher, and that the wild type IDH1 enzyme therefore continues to function optimally in normal cells while being inhibited in tumor cells. This is supported by the observation that wild type IDH1 whole body knockout mice do not exhibit an appreciable phenotype under baseline conditions (Itsumi, M., et al., IDH1 protects murine hepatocytes from endotoxin-induced oxidative stress by regulating the intracellular NADP(+)/NADPH ratio. Cell Death Differ, 2015. 22(11): p. 1837-45).

Example 3

AG-120 Inhibits Wild Type 1DH1 Enzyme Activity in an In Vitro a Cell-Based Assay Under Low Magnesium Ion Concentrations In an assay performed on pancreatic cancer cells, AG-120 demonstrated potency under low magnesium ion conditions (FIG. 4). In this experiment, an IDH assay was performed, so the activity of both IDH1 and IDH2 were measured (AG-120 does not inhibit the latter, so the impact is underestimated from the inclusion IDH2 activity). Here, at low $Mg^{2+}$ concentrations (0.08 mM, e.g., tumor microenvironment), wild type IDH inhibition was observed with 1 µM AG-120 (purple bar). However, AG-120 had no effect under normal cell culture conditions, which included 0.8 mM magnesium ion (red bar). At even lower magnesium ion concentrations (0.016 mM), inhibition was seen at 0.1 µM AG-120 dosing (green bar).

The data show that AG-120 inhibits wild type 1DH1 enzyme activity in an in vitro cell-based assay under low magnesium ion concentrations but not under standard culture magnesium ion concentrations.

Example 4

Reactive Oxygen Species (ROS) Levels are Increased in IDH1-Knockout Cells Under Low Glucose Concentrations We have previously shown that low glucose conditions induce ROS induction in pancreatic cancer cells.[8] Mechanistically, inhibiting IDH1 exacerbates this, threatening pancreatic cancer cells from the cytotoxic effects of oxidative stress.

ROS levels were measured by measuring 2',7'-dichlorodihydrofluorescein diacetate (DCFDA) or MitoSOX as previously described (Zarei et al. (2017) Cancer Res; 77(16) 4460-4471). Data herein show that genetic inhibition of wtIDH1 (i.e., IDH1-knockout) increased ROS levels (FIG. 5).

Example 5

AG-120 Induces ROS in an In Vitro Cell-Based Assay Under Low Mg Concentrations Only FIG. 6 shows that treatment of pancreatic cancer cell line (Panc1) cells with AG-120 did not induce reactive oxygen species (ROS) under standard culture conditions (25 mM glucose and 0.81 mM magnesium ion). FIG. 6 shows that AG-120 treatment under normal cell culture conditions did not result in an increase in ROS levels (red bar at 25 mM glucose). However, a surprising 3-fold increase in ROS was observed with AG-120 treatment (1 µM) under low magnesium ion concentration (zero mM magnesium ion) and low glucose concentration (2.5 mM glucose) (red bar). Importantly, these low magnesium ion and low glucose conditions were consistent with the pancreatic cancer tumor microenvironment (FIG. 6).

Example 6

AG-120 Decreased Tumor Volume and Tumor Weight of Pancreatic Xenografts

In a xenograft study (n=5 per group), oral AG-120 at 150 mg/kg (the dose used in a prior mouse study targeting mutant IDH1 tumors and FIG. 16)[3,9], FIG. 7 shows that AG-120 was remarkably potent against a wild type IDH1 pancreatic cancer (MiaPaCa2 cell line). Out of 5 xenografts per group, AG-120 was effective in reducing cancer in all cases, and completely cured the mice of cancer in 2 out 5 cases (FIG. 7). No toxicity was observed.

Example 7

Nine Mutant IDH1 Inhibitors Show Significant Inhibition of Wild Type IDH1 Isozyme in Low Magnesium (0.08 mM) in Pancreas Cell Based Assay Nine different commercial mutant IDH1 inhibitors were tested as wild type IDH1 inhibitors in a cell-based assay. The assay measures NADPH levels. Tey all showed significant inhibition of the enzyme at low magnesium (0.08 mM, FIG. 11). All compounds were dosed at 100 nM. This experiment demonstrates that under low magnesium conditions, they all also target the wild type enzyme and function as wild type IDH1 inhibitors. AG-120 is among the most active in this group.

Example 8

AG-120 (1 µM) is Lethal to Pancreatic Cancer Cells Under Low Nutrient Conditions While the drugs target the wild type enzyme at any glucose condition when magnesium levels are low, they only impact cancer cell survival when nutrients are also low. While an understanding of the invention is not required, and without limiting the invention to any particular mechanism, one potential reason for this is that wild type IDH1 is not important for cell survival when there is an abundant nutrient supply. However, when nutrients are scarce, oxidative stress is very high and the cells need an increase in IDH1-dependent NADPH synthesis to counteract the oxidative stress. FIG. 12 demonstrates this point. Under high nutrient or standard cell cultures conditions, AG-120 is ineffective at cell killing. Surprisingly, experiments performed under normal cell culture conditions containing standard magnesium and glucose concentrations would never have detected AG-120 as an important anti-cancer agent. While cells struggle to grow when nutrients are low, they are able to grow at a reduced rate. AG-120 completely abrogates any chance at growth however under these nutrient-depleted conditions (FIG. 12, colony formation assay, under low magnesium, 0.08 mM). A thermal shift assay shows stabilization of the IDH1 wild type protein at high temperatures, indicating that indeed the AG-120 compound does interact with the wild type IDH1 enzyme, again under low magnesium conditions (FIG. 13).

Example 9

AG-120 is Effective as a Monotherapy in Colon Cancer, Lung Cancer, and Ovarian Cancer The above Example 6 showed that AG-120 has anti-cancer activity in a pancreatic cancer xenograft model. Here, we show that the drug's activity is not limited to pancreatic cancer. The drug is active against cancers expressing wild type IDH1, including colon cancer (FIG. 14), lung cancer (FIG. 15) and ovarian cancer (FIG. 17).

It is important to note that in all of our experiments, the same dose of AG-120 is at least as (if not more) effective in inhibiting IDH1 wild type cancers in xenografts, as it is against IDH1 mutant cancers in xenografts at the same dose. For comparison, FIG. 16 shows a published xenograft experiment evaluating AG-120 at a comparable dose in an IDH1 mutant glioma.

Example 10

High Glucose Diet Rescues IDH1-Knockout Pancreatic Cancer Cell Growth

IDH1 knockout impairs pancreatic cancer growth in low glucose conditions. FIG. 18A B shows that IDH1−/− cells were rescued in mice by raising the intra-tumoral glucose through a high glucose diet (sugar water). This demonstrates that IDH1−/− is only important under a low glucose or nutrient poor environment, as typically faced by cancer cells, such as pancreatic cancer cells, in patients. In other words, AG-120 is expected to selectively inhibit cancer cell growth, and spare normal cells.

Example 11

Mouse Pancreatic Cancer has Low Mg (Compared to Serum)

Ivosidenib (AG-120) is potent under low magnesium and low glucose conditions, in vitro. FIG. 19 shows that AG-120 is not very effective in inhibiting wild type IDH1 enzyme activity under normal serum $Mg^{2+}$ concentrations, but below 0.4 mM, AG-120 has good efficacy.

FIG. 20 shows that pancreatic cancer cells have low concentration of $Mg^{2+}$ (0.3 mM) compared to serum (1 mM). This was a surprising discovery.

REFERENCES

1. Brody J R, Yabar C S, Zarei M, et al. Identification of a novel metabolic-related mutation (IDH1) in metastatic pancreatic cancer. Cancer Biot Ther 2016;0.
2. Zarei M, Lal S, Vaziri-Gohar A, et al. RNA-Binding Protein HuR Regulates Both Mutant and Wild-Type IDH1 in IDH1-Mutated Cancer. Mol Cancer Res 2019; 17:508-520.
3. Popovici-Muller J, Lemieux R M, Artin E, et al. Discovery of AG-120 (Ivosidenib): A First-in-Class Mutant IDH1 Inhibitor for the Treatment of IDH1 Mutant Cancers. ACS Med Chem Lett 2018; 9:300-305.
4. Urban D J, Martinez N J, Davis M I, et al. Assessing inhibitors of mutant isocitrate dehydrogenase using a suite of pre-clinical discovery assays. Sci Rep 2017; 7:12758.
5. Deng G, Shen J, Yin M, et al. Selective inhibition of mutant isocitrate dehydrogenase 1 (IDH1) via disruption of a metal binding network by an allosteric small molecule. J Biol Chem 2015; 290:762-74.
6. Seltzer M H, Rosato F E, Fletcher M J. Serum and tissue magnesium levels in human breast carcinoma. J Surg Res 1970; 10:159-62.
7. Fuhrmann A, Banisadr A, Beni P, et al. Metastatic State of Cancer Cells May Be Indicated by Adhesion Strength. Biophys J 2017; 112:736-745.
8. Zarei M, Lal S, Parker S J, et al. Posttranscriptional Upregulation of IDH1 by HuR Establishes a Powerful Survival Phenotype in Pancreatic Cancer Cells. Cancer Res 2017; 77:4460-4471.
9. Nicolay B, Narayanaswani R, Aguado E, et al. The IDH1 mutant inhibitor AG-120 shows strong inhibition of 2-H G production in an orthotopic IDH1 mutant glioma model in vivo. Society of Neuro-Oncology. San Francisco, 2017.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

I claim:

1. A method of treating cancer in a mammalian subject in need thereof, said cancer contains cancer cells characterized by presence of wild type isocitrate dehydrogenase 1 (IDH1) enzyme and absence of mutant IDH1 enzyme, the method comprising
administering to said subject a pharmaceutical composition comprising compound AG-120 having the formula

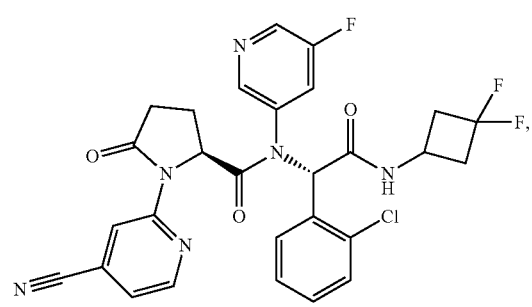

and
reducing glucose concentration in blood of said subject.

2. A method of treating cancer in a mammalian subject in need thereof, said cancer contains cancer cells characterized by presence of wild type isocitrate dehydrogenase 1 (IDH1) enzyme and absence of mutant IDH1 enzyme, the method comprising
administering to said subject a pharmaceutical composition comprising compound AG-120 having the formula

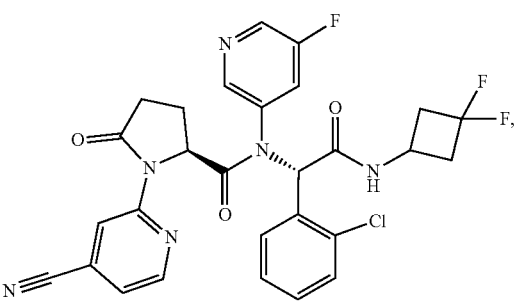 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

and
administering 2-deoxyglucose (2DG) to the subject.

3. The method of claim 1, wherein said cancer cells further have a lower Magnesium$^{2+}$ ($Mg^{2+}$) concentration compared to $Mg^{2+}$ concentration in serum.

4. The method of claim 1, said cancer comprises one or more of pancreatic cancer, colon cancer, lung cancer and ovarian cancer.

5. The method of claim 1, said wild type IDH1 enzyme is overexpressed in said cancer cells compared to non-cancerous cells, wherein said cancer cells and said non-cancerous cells are of the same cell type.

6. The method of claim 1, said cancer cells further lack mutant IDH1 gene.

7. The method of claim 1, said method further comprising administering to the subject an anti-cancer compound that reduces cancer.

8. The method of claim 2, wherein said cancer cells further have a lower Magnesium$^{2+}$ (Mg$^{2+}$) concentration compared to Mg$^{2+}$ concentration in serum.

9. The method of claim 2, said cancer comprises one or more of pancreatic cancer, colon cancer, lung cancer and ovarian cancer.

10. The method of claim 2, said wild type IDH1 enzyme is overexpressed in said cancer cells compared to non-cancerous cells, wherein said cancer cells and said non-cancerous cells are of the same cell type.

11. The method of claim 2, said cancer cells further lack mutant IDH1 gene.

12. The method of claim 2, said method further comprising administering to the subject an anti-cancer compound that reduces cancer.

13. A method of treating cancer in a mammalian subject in need thereof, said cancer contains cancer cells characterized by presence of wild type isocitrate dehydrogenase 1 (IDH1) enzyme and absence of mutant IDH1 enzyme, the method consisting of administering to said subject compound AG-120 having the formula

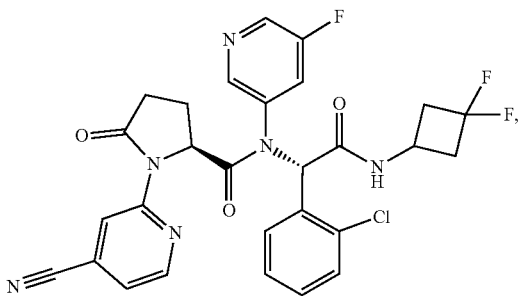 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

said pharmaceutical composition is in a therapeutic amount that reduces wild type IDH1 enzyme activity in said cancer cells.

* * * * *

SEQUENCE LISTING

```
<160> NUMBER OF SEQ ID NOS: 1

<210> SEQ ID NO 1
<211> LENGTH: 414
<212> TYPE: PRT
<213> ORGANISM: Homo sapiens

<400> SEQUENCE: 1

Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190
```

```
Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410
```